(12) United States Patent
Wagner et al.

(10) Patent No.: US 9,031,792 B2
(45) Date of Patent: *May 12, 2015

(54) METHOD OF USING A LEAD TO REGULATE PROTEIN EXPRESSION

(75) Inventors: Darrell O. Wagner, Isanti, MN (US); Haris J. Sih, Minneapolis, MN (US); Jihong Qu, Maple Grove, MN (US); Jeffrey Ross, Roseville, MN (US); Steven D. Girouard, Chagrin Falls, OH (US); Ronald W. Heil, Jr., Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1902 days.

This patent is subject to a terminal disclaimer.

(21) Appl. No.: 11/277,552

(22) Filed: Mar. 27, 2006

(65) Prior Publication Data

US 2007/0036771 A1 Feb. 15, 2007

Related U.S. Application Data

(63) Continuation of application No. 11/272,432, filed on Nov. 10, 2005, now abandoned.

(60) Provisional application No. 60/707,637, filed on Aug. 12, 2005.

(51) Int. Cl.
*G01N 33/48* (2006.01)
*A61K 48/00* (2006.01)
*A61N 1/05* (2006.01)

(52) U.S. Cl.
CPC ......... *A61K 48/0008* (2013.01); *A61K 48/0083* (2013.01); *A61N 1/05* (2013.01)

(58) Field of Classification Search
None
See application file for complete search history.

(56) References Cited

U.S. PATENT DOCUMENTS

| | | | |
|---|---|---|---|
| 3,767,437 A | 10/1973 | Cruz, Jr. et al. | |
| 4,220,152 A * | 9/1980 | Dresback | 424/439 |
| 4,559,304 A | 12/1985 | Kasai et al. | |
| 4,686,986 A | 8/1987 | Fenyo et al. | |
| 4,703,756 A | 11/1987 | Gough et al. | |
| 4,724,835 A | 2/1988 | Liss et al. | |
| 4,761,417 A * | 8/1988 | Maroko | 514/284 |
| 4,895,154 A | 1/1990 | Bartelt et al. | |
| 4,919,141 A | 4/1990 | Zier et al. | |
| 4,966,144 A | 10/1990 | Rochkind et al. | |
| 5,103,821 A | 4/1992 | King | |
| 5,130,141 A | 7/1992 | Law et al. | |
| 5,135,004 A | 8/1992 | Adams et al. | |
| 5,259,380 A | 11/1993 | Mendes et al. | |
| 5,295,947 A | 3/1994 | Muncy | |
| 5,372,133 A | 12/1994 | Hogen Esch | |
| 5,431,160 A | 7/1995 | Wilkins | |
| 5,458,620 A | 10/1995 | Adams et al. | |
| 5,486,359 A | 1/1996 | Caplan et al. | |
| 5,531,768 A | 7/1996 | Alferness | |
| 5,543,318 A | 8/1996 | Smith et al. | |
| 5,571,151 A | 11/1996 | Gregory | |
| 5,580,779 A | 12/1996 | Smith et al. | |
| 5,593,852 A | 1/1997 | Heller et al. | |
| 5,640,978 A | 6/1997 | Wong | |
| 5,693,085 A | 12/1997 | Buirge et al. | |
| 5,788,682 A | 8/1998 | Maget | |
| 5,891,558 A | 4/1999 | Bell et al. | |
| 5,913,884 A | 6/1999 | Trauner et al. | |
| 6,042,531 A | 3/2000 | Holcomb | |
| 6,063,108 A | 5/2000 | Salansky et al. | |
| 6,090,622 A | 7/2000 | Gearhart et al. | |
| 6,108,577 A | 8/2000 | Benser | |
| 6,135,976 A | 10/2000 | Tachibana et al. | |
| 6,156,028 A | 12/2000 | Prescott | |
| 6,162,211 A | 12/2000 | Tankovich et al. | |
| 6,168,590 B1 | 1/2001 | Neev | |
| 6,206,914 B1 | 3/2001 | Soykan et al. | |
| 6,210,426 B1 | 4/2001 | Cho et al. | |
| 6,234,645 B1 | 5/2001 | Borner et al. | |
| 6,245,566 B1 | 6/2001 | Gearhart et al. | |
| 6,321,100 B1 | 11/2001 | Parker | |
| 6,368,284 B1 | 4/2002 | Bardy | |
| 6,379,376 B1 | 4/2002 | Lubart | |

(Continued)

FOREIGN PATENT DOCUMENTS

EP 1919511 B1 12/2011
WO WO-02/49669 A2 6/2002

(Continued)

OTHER PUBLICATIONS

Greatbatch et al., Journal of Magnetic Resonance Imaging, 2002, vol. 16, p. 97-103.*
Hofmann et al., Proc. Natl. Acad. Sci., 1996, vol. 93, p. 5185-5190.*
Brown (Expert Opin Drug Deliv., Jan. 2005;2(1):29-42).*
Sershen et al. (Advanced Drug Delivery Reviews 54 (2002) 1225-1235).*
"U.S. Appl. No. 11/272,432, Non-Final Office Action mailed Mar. 4, 2009", 8 pgs.
"U.S. Appl. No. 11/272,432, Response filed Jul. 6, 2009 to Non-Final Office Action mailed Mar. 4, 2009", 23 pgs.
"Cytochrome P450", [online]. [retrieved Jan. 16, 2007]. Retrieved from the Internet: <URL: http://www.anaesthetist.com/physiol/basics/metabol/cyp/Findex.htm#cyp.htm>, (Date of First Publication: Jun. 25, 2000; Date of Last Update: Oct. 24, 2006), 8 pgs.
"European Application Serial No. 06787153.3, Communication mailed Jun. 5, 2008", 5 pgs.
"European Application Serial No. 06787153.3, Response filed Dec. 5, 2008 to Communication mailed June. 5, 2008", 11 pgs.
"Heme Oxygenase-2 (HO-2)", [online]. [retrieved Jan. 16, 2007]. Retrieved from the Internet: <http://www.4adi.com/data/enzyme/ho25.html>, (Copyright © 1996-2005), 2 pgs.

(Continued)

*Primary Examiner* — Pablo S Whaley
(74) *Attorney, Agent, or Firm* — Schwegman Lundberg & Woessner, P.A.

(57) ABSTRACT

A system and device are provided which include a gene regulatory system controlling expression of one or more expression cassettes present in or released by the device, by emitting one or more stimulations. An expression cassette includes a regulatable transcription control element that is responsive to the emitted stimulations linked to an open reading frame of interest. The system optionally includes a sensor to sense a parameter indicative of a need, a telemetry module to receive an external command, or a programmable device, for regulating gene expression of the open reading frame.

21 Claims, 3 Drawing Sheets

(56) References Cited

U.S. PATENT DOCUMENTS

| | | |
|---|---|---|
| 6,443,978 B1 | 9/2002 | Zharov |
| 6,494,900 B1 | 12/2002 | Salansky et al. |
| 6,520,981 B1 | 2/2003 | LaMuraglia |
| 6,602,275 B1 | 8/2003 | Sullivan |
| 6,608,038 B2 | 8/2003 | Caplan et al. |
| 6,692,517 B2 | 2/2004 | Cho et al. |
| 6,733,996 B2 | 5/2004 | Froehlich et al. |
| 6,759,236 B1 | 7/2004 | Fung et al. |
| 6,801,805 B2 | 10/2004 | Stokes et al. |
| 6,810,286 B2 | 10/2004 | Donovan et al. |
| 6,811,565 B2 | 11/2004 | Denton et al. |
| 6,824,561 B2 | 11/2004 | Soykan et al. |
| 6,827,690 B2 | 12/2004 | Bardy |
| 6,830,580 B2 | 12/2004 | Neuberger |
| 6,843,778 B2 | 1/2005 | Foldes |
| 6,913,577 B2 | 7/2005 | Bardy |
| 6,919,207 B2 | 7/2005 | Goodman et al. |
| 7,072,711 B2 | 7/2006 | Girouard et al. |
| 7,299,087 B2 | 11/2007 | Bardy |
| 7,437,191 B2 | 10/2008 | Pastore et al. |
| 7,460,906 B2 | 12/2008 | Libbus |
| 7,486,991 B2 | 2/2009 | Libbus et al. |
| 2001/0000802 A1 | 5/2001 | Soykan et al. |
| 2002/0010492 A1 | 1/2002 | Donovan et al. |
| 2002/0065239 A1 | 5/2002 | Caplan et al. |
| 2002/0065243 A1 | 5/2002 | Fung et al. |
| 2002/0099026 A1 | 7/2002 | Goodman et al. |
| 2002/0110804 A1 | 8/2002 | Stanton et al. |
| 2002/0110910 A1 | 8/2002 | Gwathmey et al. |
| 2003/0028222 A1 | 2/2003 | Stahmann |
| 2003/0044802 A1 | 3/2003 | Sayler et al. |
| 2003/0073235 A1 | 4/2003 | Lagarias et al. |
| 2003/0148968 A1 | 8/2003 | Hammond et al. |
| 2003/0175680 A1 | 9/2003 | Allard et al. |
| 2003/0204206 A1* | 10/2003 | Padua et al. ............ 607/2 |
| 2004/0038400 A1 | 2/2004 | Froehlich et al. |
| 2004/0048286 A1 | 3/2004 | Lee |
| 2004/0111132 A1 | 6/2004 | Shenderova et al. |
| 2004/0215307 A1 | 10/2004 | Michels et al. |
| 2004/0249423 A1 | 12/2004 | Savage |
| 2004/0260367 A1 | 12/2004 | De Taboada et al. |
| 2005/0005923 A1 | 1/2005 | Herrin |
| 2005/0025752 A1 | 2/2005 | Kutryk et al. |
| 2005/0059153 A1 | 3/2005 | George et al. |
| 2005/0080465 A1 | 4/2005 | Zelickson et al. |
| 2005/0096701 A1 | 5/2005 | Donovan et al. |
| 2005/0130136 A1 | 6/2005 | Lee |
| 2005/0143779 A1 | 6/2005 | Libbus |
| 2005/0149129 A1 | 7/2005 | Libbus et al. |
| 2005/0192637 A1 | 9/2005 | Girouard et al. |
| 2006/0206158 A1 | 9/2006 | Wu et al. |
| 2006/0247686 A1 | 11/2006 | Girouard et al. |
| 2007/0036770 A1 | 2/2007 | Wagner et al. |
| 2007/0112344 A1 | 5/2007 | Keilman |
| 2007/0282380 A1 | 12/2007 | Brooke et al. |
| 2008/0058661 A1 | 3/2008 | Bardy |
| 2008/0058881 A1 | 3/2008 | Wagner et al. |
| 2008/0058905 A1 | 3/2008 | Wagner |
| 2008/0076836 A1 | 3/2008 | Wagner et al. |
| 2008/0125836 A1 | 5/2008 | Streeter et al. |
| 2008/0132972 A1 | 6/2008 | Shuros et al. |
| 2009/0048641 A1 | 2/2009 | Libbus |

FOREIGN PATENT DOCUMENTS

| | | | |
|---|---|---|---|
| WO | WO-02/49714 A2 | | 6/2002 |
| WO | WO-02/094997 A2 | | 11/2002 |
| WO | WO/2005/028024 | * | 3/2005 |
| WO | WO-2005/028024 A1 | | 3/2005 |
| WO | WO-2005/084751 A2 | | 9/2005 |
| WO | WO-2007/021413 A2 | | 2/2007 |

OTHER PUBLICATIONS

"Heme Oxygenases", [online]. [retrieved Jan. 16, 2007]. Retrieved from the Internet: <URL: http://web.archive.org/web/20060427204923/http://www.sacs.ucsf.edu/home/Ortiz/res-ho.htm, (2006), 2 pgs.

"International Application Serial No. PCT/US2006/027209, International Search Report mailed Feb. 5, 2007", 5 pgs.

"International Application Serial No. PCT/US2006/027209, Written Opinion mailed Feb. 5, 2007", 8 pgs.

Dickson, E. W, et al., "Preconditioning at a Distance in the Isolated Rabbit Heart", *Academic Emergency Medicine*, 7(4), (2000), 311-317.

KOç, O. N., et al., "Akt helps stem cells heal the heart", *Nature Medicine*, 9(9), (2003), 1109-1110.

Lin, H., et al., "Regulating Genes with Electromagnetic Response Elements", *Journal of Cellular Biochemistry*, 81, (2001), 143-148.

Lin, H., et al., "Specific Region of the c-myc Promoter is Responsive to Electric and Magnetic Fields", *Journal of Cellular Biochemistry*, 54, (1994), 281-288.

Mangi, A. A., et al., "Mesenchymal stem cells modified with Akt prevent remodeling and restore performance of infarcted hearts", *Nature Medicine*, 9(9), (2003), 1195-1201.

Murry, C. E., et al., "Preconditioning with ischemia: a delay of lethal cell injury in ischemic myocardium", *Circulation*, 74(5), (1986), 1124-1136.

Patberg, K. W., et al., "Cardiac Memory Is Associated With Decreased Levels of the Transcriptional Factor CREB Modulated by Angiotensin II and Calcium", *Circulation Research*, vol. 93, (2003), 472-478.

Przyklenk, K., et al., "Cardioprotection 'Outside the Box'—The evolving paradigm of remote preconditioning", *Basic Res. Cardiol.*, 98(3), (2003), 149-157.

Radisic, M., et al., "Functional assembly of engineered myocardium by electrical stimulation of cardiac myocytes cultured on scaffolds", *Proc Natl Acad Sci U S A.*, 101(52), (Dec. 28, 2004), 18129-18134.

Rubenstrunk, A., et al., "Transcriptional Activation of the Metallothionein I Gene by Electric Pulses in vivo: Basis for the Development of a New Gene Switch System", *The Journal of Gene Medicine*, 5, (2003), 773-783.

Slebos, Dirk-Jan, et al., "Heme oxygenase-1 and carbon monoxide in pulmonary medicine", *Respir Res.*, 4:7, (Aug. 7, 2003), 1-13.

"U.S. Appl. No. 11/272,432, Final Office Action mailed Oct. 29, 2009", 10 Pgs.

"U.S. Appl. No. 11/272,432, Preliminary Amendment filed Feb. 21, 2006", 6 pgs.

"U.S. Appl. No. 11/272,432, Response filed Feb. 9, 2010 to Final Office Action mailed Oct. 21, 2009", 12 pgs.

"U.S. Appl. No. 11/469,767, Non-Final Office Action mailed Apr. 22, 2010", 15 pgs.

Van Der Giessen, W. J, et al., "Marked inflammatory sequelae to implantation of biodegradable and nonbiodegradable polymers in porcine coronary arteries.", *Circulation*, 94(7), (Oct. 1, 1996), 1690-7.

"U.S. Appl. No. 11/272,432, Response filed Aug. 2, 2010 to Non Final Office Action mailed Apr. 2, 2010", 28 pgs.

"Japanese Application Serial No. 2008-526020, Amended Claims filed Jul. 8, 2009", (w/ English Translation of Amended Claims, 15 pgs.

"U.S. Appl. No. 11/272,432, Final Office Action mailed Nov. 24, 2010", 18 pgs.

"U.S. Appl. No. 11/272,432, Response filed Feb. 24, 2011 to Final Office Action mailed Nov. 24, 2010", 15 pgs.

"Japanese Application Serial No. 2008-526020, Office Action mailed Nov. 2, 2011", w/ English Translation, 5 pgs.

"Japanese Application Serial No. 2008-526020, Response filed Jan. 31, 2012 to Office Action mailed Nov. 2, 2011", With English Claims, 40 pgs.

Van Breugel, H. H. F. I., et al., "Power density and exposure time of He-Ne laser irradiation are more important than total energy dose in photo-biomodulation of human fibroblasts in vitro.", Lasers in Surgery and Medicine, 12(5), (1992), 528-537.

"U.S. Appl. No. 11/272,432, Non Final Office Action mailed Sep. 23, 2013", 20 pgs.

"U.S. Appl. No. 11/272,432, Response filed Dec. 19, 2013 to Non Final Office Action mailed Sep. 23, 2013", 19 pgs.

(56) References Cited

OTHER PUBLICATIONS

"U.S. Appl. No. 11/272,432, Final Office Action mailed Apr. 2, 2014", 13 pgs.

"U.S. Appl. No. 11/843,573, Final Office Action mailed Aug. 20, 2014", 22 pgs.

"U.S. Appl. No. 11/843,573, Non Final Office Action mailed Apr. 29, 2014", 20 pgs.

"U.S. Appl. No. 11/843,573, Response filed Jun. 24, 2014 to Non Final Office Action mailed Apr. 4, 2014", 13 pgs.

Lam, et al., "Laser stimulation of collagen synthesis in human skin fibroblast cultures", Lasers in the Life Sciences 1, (1986), 61-77.

Sato, et al., "A light-switchable gene promoter system", Nature Biotechnology 20(10), Published online Sep. 3, 2002, 1041-1044.

Tuan, et al., "In vitro fibroplasia: matrix contraction, cell growth, and collagen production of fibroblasts cultured in fibrin gels", Exp Cell Res 223, (1996), 127-134.

* cited by examiner

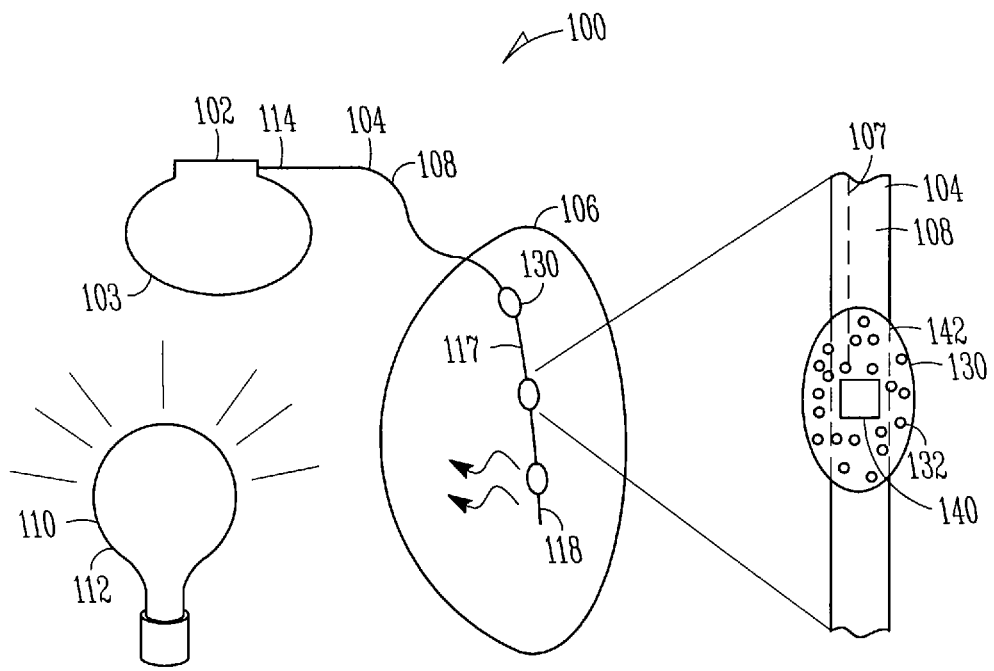
FIG. 1  FIG. 2A
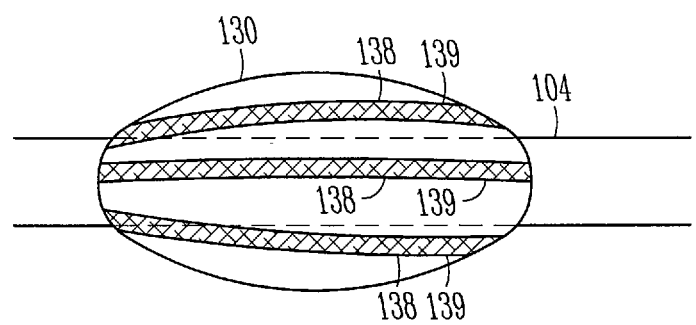
FIG. 2B

METHOD OF USING A LEAD TO REGULATE PROTEIN EXPRESSION

CROSS-REFERENCE TO RELATED APPLICATION(S)

This application is a continuation of U.S. application Ser. No. 11/272,432, filed on Nov. 10, 2005, now abandoned which claims the benefit of U.S. Provisional Application No. 60/707,637, filed on Aug. 12, 2005, under 35 U.S.C. §119(e), both of which are hereby incorporated by reference.

FIELD OF THE INVENTION

This invention relates generally to gene therapy, for example, the use of genetically modified cells or recombinant gene therapy vectors, and particularly, but not by way of limitation, to method and apparatus for direct regulation of gene expression.

BACKGROUND

The heart is the center of a person's circulatory system. It includes an electromechanical system performing two major pumping functions. The left portions of the heart draw oxygenated blood from the lungs and pump it to the organs of the body to provide the organs with their metabolic needs for oxygen. The right portions of the heart draw deoxygenated blood from the organs and pump it into the lungs where the blood gets oxygenated. The body's metabolic need for oxygen increases with the body's physical activity level. The pumping functions are accomplished by contractions of the myocardium (heart muscles). In a normal heart, the sinoatrial node, the heart's natural pacemaker, generates electrical impulses, known as action potentials, that propagate through an electrical conduction system to various regions of the heart to excite myocardial tissues in these regions. Coordinated delays in the propagations of the action potentials in a normal electrical conduction system cause the various regions of the heart to contract in synchrony such that the pumping functions are performed efficiently.

A blocked or otherwise damaged electrical conduction system causes the myocardium to contract at a rhythm that is too slow, too fast, and/or irregular. Such an abnormal rhythm is generally known as arrhythmia. Arrhythmia reduces the heart's pumping efficiency and hence, diminishes the blood flow to the body. A deteriorated myocardium has decreased contractility, also resulting in diminished blood flow. A heart failure patient usually suffers from both a damaged electrical conduction system and a deteriorated myocardium. The diminished blood flow results in insufficient blood supply to various body organs, preventing these organs to function properly and causing various symptoms. For example, in a patient suffering acute decompensated heart failure, an insufficient blood supply to the kidneys results in fluid retention and edema in the lungs and peripheral parts of the body, a condition referred to as decompensation. Without effective treatment, acute decompensated heart failure cause rapid deterioration of the cardiovascular and general health and significantly shortened life expectancy. Treatments for arrhythmias and heart failure include, but are not limited to, electrical therapy such as pacing and defibrillation therapies, drug therapies, and biological therapies including gene-based therapies.

Gene-based therapies include the delivery of therapeutic genes to targeted cells and in some cases, the use of regulatable systems. For gene-based therapies which require expression of sequences in vectors, a promoter is linked to the sequence to be expressed. Strong viral promoters can drive a high level of expression in a wide range of tissues and cells, however, constitutive expression is an open loop system and the encoded gene product may induce cellular toxicity or tolerance, or down regulation of expression through negative feedback.

One strategy to regulate the expression of target genes employs endogenous regulatable elements, and another strategy employs exogenous inducible gene expression systems. For example, heat-shock-induced loci have been used to regulate the expression of a heterologous gene in mammalian cells, and hypoxia-inducible cis-acting sequences from the erythropoietin gene allow a transcriptional response by hypoxia-inducible transcription factor (HIF-I).

What is needed is a device useful to control expression of gene therapy vectors, including those in genetically modified cells, e.g., to treat cardiovascular conditions.

SUMMARY OF THE INVENTION

The invention provides for an implantable device that is adapted to control the expression of exogenous or endogenous genes transferred to a host mammal (recipient) by the device, which genes are optionally retained in the device while the device is implanted, genes useful to prevent, inhibit or treat various conditions including cardiovascular conditions. In particular, the invention provides for the therapeutic effect of secretable factors by utilizing an implantable device to turn on and control (regulate) the expression of genes delivered by and optionally retained in the device. In one embodiment, the implantable device is a lead, the body of which is modified to contain one or more hollow depositories ("gene depositories") adapted for delivery of donor cells including unmodified donor cells which express or can be induced to express a desirable gene product, for instance, HO-1 or PAI-2, or recombinant virus or donor cells having an expression cassette ("genetically modified donor cells") for expression of a desirable gene product. The gene depositories include a porous, biocompatible and substantially nonbiodegradable material that does not permit the transmission of cells, e.g., prokaryotic or eukaryotic cells, but does permit the passage of soluble cellular factors, i.e., factors expressed by the cells, across the material. In one embodiment, the porous, biocompatible and substantially nonbiodegradable material permits passage of virus delivered by a gene depository to a host mammal, while in other embodiments the porous, biocompatible and substantially nonbiodegradable material does not permit passage of virus. For instance, in one embodiment, the material may have a pore size selected to allow the passage of viruses with a diameter of greater than about 20 nm, e.g., greater than about 50, 100 or 200 nm, depending on the virus employed. In another embodiment, the porous, biocompatible and substantially nonbiodegradable material may have a pore size that prevents or inhibits the passage of virus and cells but permits the passage of soluble factors across the material.

The one or more gene depositories may protrude from the lead body (a "nodule"), have an outer diameter substantially the same as the lead body, or recess within the lead body, or any combination thereof. The recombinant virus, e.g., replication incompetent virus, or donor cells, e.g., genetically modified donor cells, may be introduced to the one or more gene depositories prior to or after implantation. For instance, the gene depositories may be loaded with recombinant virus or donor cells prior to implantation of the implantable device, so that the expression cassette is transferred into the mammal when the implantable device, e.g., a lead, having the gene depository, is introduced to the mammal. Alternatively, the gene depositories may be loaded with recombinant virus or donor cells after device implantation.

Recombinant virus or genetically modified donor cells for use with the implantable device contain an expression cassette that has a regulatable transcription control element operably linked to an open reading frame of interest, the expression of which open reading frame in a mammal has a desirable (beneficial) effect. Donor cells which are not genetically modified for use with the implantable device express a gene product with a desirable (beneficial) effect, where the native (endogenous) gene includes a regulatable transcriptional control element linked to an open reading frame. In one embodiment, the regulatable transcriptional control element is regulated by light or an electric field. In one embodiment, the open reading frame encodes a gene product which is secreted (released into the extracellular environment) from donor cells which express the gene product, and which gene product is capable of passing through the porous, biocompatible and substantially nonbiodegradable material that forms at least a part of a gene depository. In another embodiment, the gene product alters, e.g., increases, expression of one or more other gene products in the donor cells, which one or more other gene products are released, e.g., secreted, from the cells and pass through the porous, biocompatible and substantially nonbiodegradable material. Therefore, in one embodiment, the beneficial effect of the expression of the open reading frame is direct, e.g., the expression results in a therapeutic soluble factor(s), while in another embodiment, the beneficial effect of the expression of the desirable open reading frame is indirect, e.g., the encoded gene product alters the expression of at least one other gene encoding a soluble factor in the donor cells, while in yet another embodiment the expression of the open reading yields a soluble factor which alters the expression of one or more genes in host cells, thereby resulting in a soluble factor(s) which has a beneficial effect on cells in the host.

To control the expression of the desirable gene(s) present in a gene depository, the implantable device also includes at least one gene regulatory stimulator that is associated the one or more gene depositories having the recombinant virus, donor cells which are not genetically modified or genetically modified donor cells. In one embodiment, one or more gene regulatory stimulators are associated with a gene depository. In one embodiment, one or more gene regulatory stimulators are outside of and are coupled adjacent or near a gene depository. In one embodiment, a gene regulatory stimulator is disposed adjacent or near two or more adjacent gene depositories. In one embodiment, the expression of the open reading frame in the expression cassette or endogenous gene is increased after the regulatory stimulation is delivered (e.g., emitted) and optionally continues, at least for a period of time, after the regulatory stimulation ceases. In one embodiment, after the regulatory stimulation ends, the expression of the open reading frame decreases, e.g., to a lower level, or ceases, e.g., to pre-stimulation delivery levels.

The invention further provides a system. The system includes an implantable medical device such as a lead having one or more gene regulatory stimulators. The gene regulatory stimulators emit a regulatory stimulation capable of regulating a regulatable transcription control element in an expression cassette having the regulatable transcriptional control element operably linked to an open reading frame of interest or an endogenous gene having the regulatable transcriptional control element. The implantable device, for instance, a lead, also includes one or more gene depositories adapted for transfer of recombinant virus having an expression cassette, or transfer and retention of donor cells, e.g., donor cells having an expression cassette, by the implantable device, which gene depositories are disposed on the body of the implantable device. At least one gene regulatory stimulator is associated with the at least one gene depository so that a regulatory stimulation emitted from the gene regulatory stimulation device can alter expression of the desirable open reading frame. For example, a light emitting diode (LED) may be a gene regulatory stimulator and more than one LED may be associated with each gene depository. The one or more gene depositories include a porous, biocompatible and substantially nonbiodegradable material that permits the exchange of soluble factors such as secreted, excreted or otherwise cell-free (soluble) proteins or glycoproteins, or in another embodiment virus, across the material but does not permit transmission of cells, i.e., donor cells delivered to the mammal by the gene depository are retained in the device and host cells are excluded from the gene depository. In one embodiment, the system further includes a sensor to sense a physiological parameter indicative of a predetermined condition. In one embodiment, the system further includes a controller coupled to the sensor and one or more of the gene regulatory stimulators, the controller adapted to control the emission of the regulatory stimulation based on at least the sensed physiological parameter. In another embodiment, the system further includes a controller coupled to a telemetry module, the telemetry module adapted to receive an external command, and the controller adapted to control the emission of the regulatory stimulation based on at least the external command. In another embodiment, the system further includes a controller coupled to a programmable device, the controller adapted to control the emission of the regulatory stimulation based on a predetermined program executed by the programmable device.

Also provided is a lead. The lead includes one or more gene depositories each adapted for delivery of recombinant virus, cells, or both, disposed along the lead body. The one or more gene depositories include a porous biocompatible and substantially nonbiodegradable material that permits the exchange of soluble factors and optionally virus but does not permit transmission of cells across the material. The one or more gene depositories contain recombinant virus having an expression cassette comprising a regulatable transcription control element operably linked to an open reading frame of interest or donor cells, e.g., genetically modified donor cells having an expression cassette comprising a regulatable transcription control element operably linked to an open reading frame of interest. The lead also includes one or more gene regulatory stimulators associated with the gene depository, which gene regulatory stimulator emits a regulatory stimulation capable of regulating a regulatable transcription control element in the expression cassette.

Further provided is a method of preparing a lead of the invention. The method includes introducing to one or more gene depositories in a lead of the invention, recombinant virus, such as replication incompetent virus, or donor cells, e.g., genetically modified donor cells. In one embodiment, the recombinant virus is dispersed or contained in a biodegradable matrix or capsule, for example, one formed from a polymer. For instance, recombinant virus may be dispersed or contained in a hydrogel, alginate, polyglycol acid (PGA), polylactic acid (PLA), co-polymers of PGA and PLA, poly (ether ester), polyethylene glycol (PEG), or block copolymers of PEG and poly(butylene terephthalate). In one embodiment, the virus containing biodegradable matrix or particle has a half-life of about 1 to 60 days, e.g., a half-life of about 14 to 30 days.

Also provided is a method of using the system or lead of the invention. The method includes providing to a mammal having the system or lead of the invention, and delivering a regulatory stimulation from the one or more gene regulatory stimulation devices in an amount effective to regulate the regulatable transcription control element, thereby regulating the gene product encoded by the open reading frame linked to the regulatable transcription control element. In one embodiment, the mammal is at risk of or has a cardiac condition and the open reading frame of interest in the expression cassette is selected so that expression of the open reading frame in the mammal prevents, inhibits or treats the condition or at least one symptom thereof. In one embodiment, the method includes sensing a physiological parameter indicative of a predetermined cardiac condition in a mammal having a lead of the invention and delivering a regulatory stimulation from the one or more gene regulatory stimulation devices in the lead in response to at least the sensed physiological parameter. In another embodiment, a regulatory stimulation is delivered from the one or more gene regulatory stimulation devices in the lead in response to a command, e.g., an external command or one from an implanted programmable device.

The invention thus provides a method of utilizing an implantable device for maintaining control of genetically modified donor cells, nongenetically modified donor cells or recombinant virus that express a gene(s) which directly or indirectly yields a soluble factor useful to inhibit or treat cardiac or other organ diseases. For embodiments which employ donor cells, e.g., genetically modified donor cells, the expression of the soluble factor(s) in the body occurs only as long as the device is implanted. For embodiments which employ recombinant virus, a viral vector which is not maintained in the host for extended periods of time, e.g., the virus does not integrate into the host genome or is not maintained extrachromosomally, and optionally is not lytic, may be employed to provide for limited duration of expression of the soluble factor(s). The invention thus provides for control of at least the initial location of the soluble factor(s), the timing of the expression of the factor(s), and optionally the level or amount of factor(s).

BRIEF DESCRIPTION OF THE DRAWINGS

The drawings illustrate generally, by way of example, but not by way of limitation, various embodiments discussed in the present document. The drawings are for illustrative purposes only and are not drawn to scale.

FIG. 1 illustrates a schematic view of a system in accordance with at least one embodiment.

FIG. 2A illustrates an elevational view of a portion of a lead in accordance with at least one embodiment.

FIG. 2B illustrates an elevational view of a portion of a lead in accordance with at least one embodiment.

DETAILED DESCRIPTION OF THE INVENTION

Figure 3:
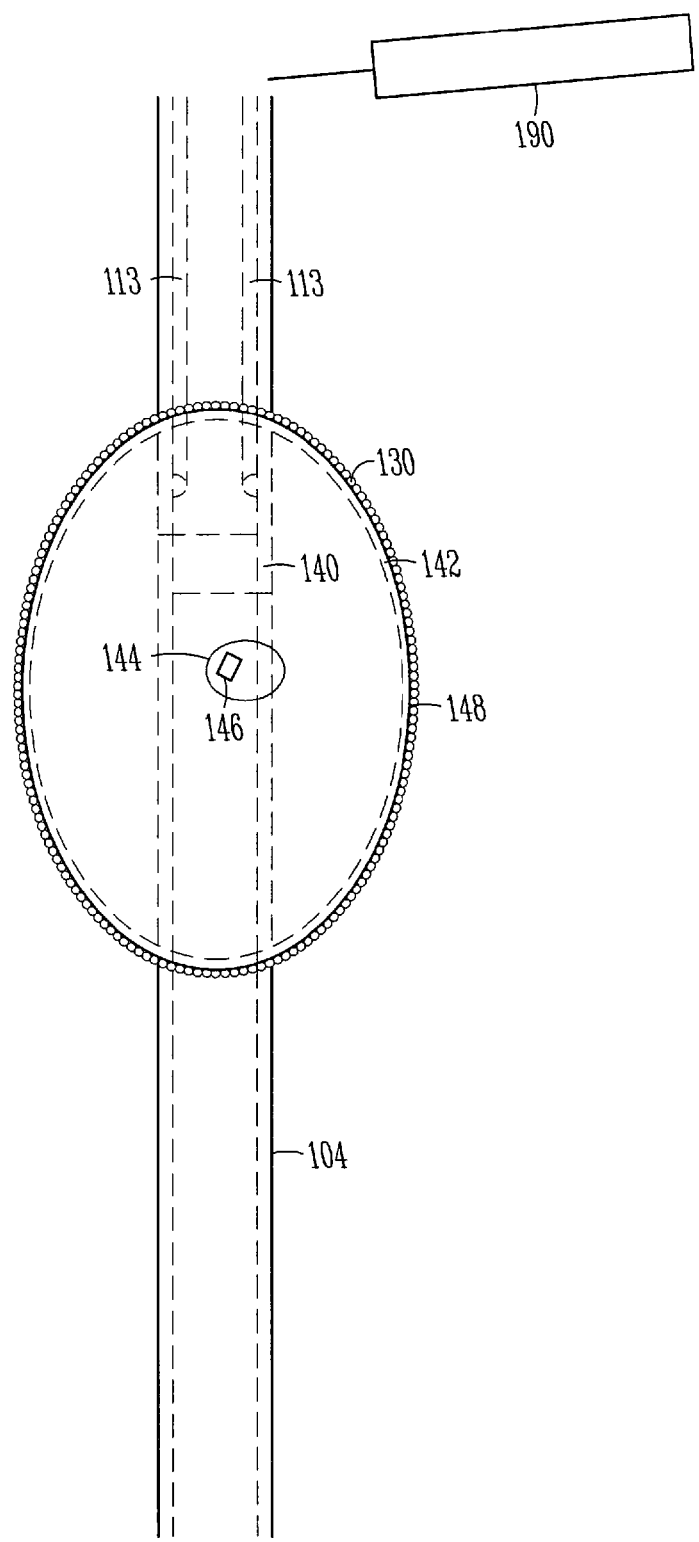
FIG. 3 illustrates an elevational view of a portion of a lead in accordance with at least one embodiment.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

General Overview

This document describes, among other things, methods and apparatus for the spatial, temporal and/or conditional control of gene expression from one or more exogenous genes (an expression cassette) or endogenous genes delivered by and optionally retained in an implantable device. The expression of the exogenous or endogenous gene in vivo prevents, inhibits or treats at least one symptom of a particular condition. In one embodiment, the condition is a cardiac condition and the expression of the exogenous or endogenous gene(s) delivered by or present in the implanted device in an animal, such as a mammal, having or at risk of the cardiac condition, beneficially alters at least one symptom of the condition. In one embodiment, the gene includes at least one open reading frame encoding a gene product operably linked to at least one regulatable transcription control element. The device of the invention may deliver one or more stimulations including, but not limited to, light of a particular wavelength or a range of wavelengths, light of a particular energy, an electric field, or other forms of temperature or matter, which stimulation is recognized by the regulatable transcription control element. A regulatable transcriptional control element includes a promoter, e.g., an inducible or repressible promoter, an enhancer, or a combination thereof.

In one embodiment, the gene product encoded by the open reading frame is a protein or glycoprotein which is secreted or otherwise released from a cell, or a transcription factor which binds to a promoter linked to an open reading frame for a protein or glycoprotein which is secreted or otherwise released from a cell, factors including, but not limited to, an angiogenic protein, a growth factor, e.g., vascular endothelial growth factor (VEGF), a differentiation factor, a survival factor, such as a member of the bcl-2 family, Akt or a homolog or ortholog thereof, a cytokine or other gene product with beneficial properties, for instance, heme oxygenase, or a protease inhibitor, e.g., a serpin such as PAI-2 (plasminogen activator inhibitor-2).

The gene of interest may be present in a recombinant virus, isolated nucleic acid or donor cells. In one embodiment, donor cells, e.g., autologous cells, are genetically modified for use in the system of the invention ex vivo by introducing an expression cassette containing a regulatable transcription control element linked to a desirable open reading frame, to those cells. In yet another embodiment, donor cells are genetically modified in vivo, for instance, by employing recombinant virus and donor cells. The recombinant virus, recombinant nucleic acid, genetically modified donor cells or donor cells which are not genetically modified are introduced to one or more depositories formed at least in part of a porous, biocompatible and substantially nonbiodegradable material, such as a membrane or mesh, that permits relatively small molecules to enter or exit the depositories but does not permit entry of host (endogenous) cells or exit of donor cells.

To control expression of the gene(s) in the implanted device, the implantable device includes a gene regulatory stimulation device which emits a stimulation, the amount and/or strength (i.e., amplitude) of which alters expression, e.g., induces expression, of the open reading frame that is operably linked to the regulatable transcription control element. Thus, the gene regulatory stimulation device in the systems and methods of the invention provides for temporal and/or conditional dosing of the gene product encoded by the open reading frame(s) in a mammal.

In one embodiment, the invention provides for a system having a lead with one or more gene depositories positioned at one or more sites along the lead body. In one embodiment, the device is part of a transvenous system. The gene depository may contain autologous cells, for instance, genetically modified autologous cells having an expression cassette, with a regulatable transcription control element, e.g., a promoter, that is capable of regulating expression of a linked open reading frame. The gene depository has a porous membrane for inflow of nutrient media and outflow of expressed soluble factors. The system also includes a stimulation source for gene stimulation within a confined space (a gene regulatory stimulator) which is in close proximity to the gene depository.

The systems and methods of the invention may be used to prevent, inhibit or treat one or more symptoms of any condition amenable to treatment, prophylactic or otherwise, by expression of soluble factors. In one embodiment, the systems of the invention are useful to treat, inhibit or prevent one or more symptoms of a cardiovascular condition. Cardiovascular conditions include but are not limited to atrial arrhythmias, ventricular arrhythmias, myocardial infarction (MI), heart failure including congestive heart failure, reentrant tachycardias, dysfunctional cardiac sinus tissue, diastolic dysfunction, ischemic heart disease, angina, dilated cardiomyopathy, atherosclerosis, vulnerable plaque, and hypertension, as well as cardiac comorbidities such as stroke, metabolic syndrome, diabetes, obesity apnea. For instance, a system of the invention may be employed to enhance cell growth in a cardiac region impacted by MI or post MI conditioning in a cardiac region at the time of reperfusion. However, the systems of the invention are not limited to cardiovascular conditions, as the lead can deliver any gene to prevent, inhibit or treat a disease or condition associated with that gene.

Thus, this document discusses a gene expression regulatory system that includes a lead which may be a portion of, or being coupled to, a system which may include other implantable medical devices. In one embodiment, the implantable medical device detects a predetermined condition indicative of a need for a therapy. In response, the implanted gene regulatory stimulator in the lead delivers one or more stimulations. In one further embodiment, the gene expression regulatory therapy is performed in conjunction with electrical therapy, such as pacing therapy. One specific example of an implantable medical device for use with a lead of the invention is an implantable cardiac rhythm management (CRM) device. Several embodiments are presented below to provide examples of different therapy apparatus and method.

Definitions

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a sequence of interest for gene therapy. Vectors include, for example, transposons and other site-specific mobile elements, viral vectors, e.g., adenovirus, adeno-associated virus (AAV), poxvirus, papillomavirus, lentivirus, herpesvirus, foamyvirus and retrovirus vectors, and including pseudotyped viruses, liposomes and other lipid-containing complexes, and other macromolecular complexes capable of mediating delivery of a polynucleotide to a host cell, e.g., DNA coated gold particles, polymer-DNA complexes, liposome-DNA complexes, liposome-polymer-DNA complexes, virus-polymer-DNA complexes, e.g., adenovirus-polylysine-DNA complexes, and antibody-DNA complexes. Vectors can also comprise other components or functionalities that further modulate gene delivery and/or gene expression, or that otherwise provide beneficial properties to the cells to which the vectors will be introduced. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described.

"Gene delivery," "gene transfer," and the like as used herein, are terms referring to the introduction of an exogenous polynucleotide (sometimes referred to as a "transgene"), e.g., via a recombinant virus, into a host cell or by a genetically modified donor cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, iontophoresis, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the cell if integrated into the genome or maintained extrachromosomally. Such a transgene may include a gene which is partly or entirely heterologous (i.e., foreign) to the transgenic organism, or may represent a gene homologous to an endogenous gene of the organism.

By "transgenic cell" or "genetically modified cell" is meant a cell containing a transgene. For example, a stem cell transformed with a vector containing an expression cassette can be used to produce a population of cells having altered phenotypic characteristics.

The term "wild-type" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "transduction" denotes the delivery of a polynucleotide to a recipient cell either in vivo or in vitro, via a viral vector and preferably via a replication-defective viral vector, such as via a recombinant AAV.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation stimulations are located 3' or downstream of the coding region.

A "gene," "polynucleotide," "coding region," or "sequence" which "encodes" a particular gene product, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. Thus, a gene includes a polynucleotide which may include a full-length open reading frame which encodes a gene product (sense orientation) or a portion thereof (sense orientation) which encodes a gene product with substantially the same activity as the gene product encoded by the full-length open reading frame, the complement of the polynucleotide, e.g., the complement of the full-length open reading frame (antisense orientation) and optionally linked 5' and/or 3' noncoding sequence(s) or a portion thereof, e.g., an oligonucleotide, which is useful to inhibit transcription, stability or translation of a corresponding mRNA. A transcription termination sequence will usually be located 3' to the gene sequence.

An "oligonucleotide" includes at least 7 nucleotides, preferably 15, and more preferably 20 or more sequential nucleotides, up to 100 nucleotides, either RNA or DNA, which correspond to the complement of the non-coding strand, or of the coding strand, of a selected mRNA, or which hybridize to the mRNA or DNA encoding the mRNA and remain stably bound under moderately stringent or highly stringent conditions, as defined by methods well known to the art, e.g., in Sambrook et al., A Laboratory Manual, Cold Spring Harbor Press (1989).

The term "control elements" refers collectively to promoter regions, polyadenylation stimulations, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence. Thus, a "promoter," refers to a polynucleotide sequence that controls transcription of a gene or coding sequence to which it is operably linked. A large number of promoters, including constitutive, inducible and repressible promoters, from a variety of different sources, are well known in the art.

By "enhancer element" is meant a nucleic acid sequence that, when positioned proximate to a promoter, confers increased transcription activity relative to the transcription activity resulting from the promoter in the absence of the enhancer domain. Hence, an "enhancer" includes a polynucleotide sequence that enhances transcription of a gene or coding sequence to which it is operably linked. A large number of enhancers, from a variety of different sources are well known in the art. A number of polynucleotides which have promoter sequences (such as the commonly-used CMV promoter) also have enhancer sequences.

"Operably linked" refers to a juxtaposition, wherein the components so described are in a relationship permitting them to function in their intended manner. By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. Thus, a stimulation or targeting peptide sequence is operably linked to another protein if the resulting fusion is secreted from a cell as a result of the presence of a secretory stimulation peptide or into an organelle as a result of the presence of an organelle targeting peptide.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. An "animal" includes vertebrates such as mammals, avians, amphibians, reptiles and aquatic organisms including fish.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination stimulation, may also be included.

The term "exogenous," when used in relation to a protein, gene or nucleic acid, e.g., polynucleotide, in a cell or organism refers to a protein, gene, or nucleic acid which has been introduced into the cell or organism by artificial or natural means, or in relation to a cell refers to a cell which was isolated and subsequently introduced to other cells or to an organism by artificial or natural means (a "donor" cell). An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide, polypeptide or virus refers to a nucleic acid sequence, peptide, polypeptide or virus that is identified and separated from at least one contaminant nucleic acid, polypeptide, virus or other biological component with which it is ordinarily associated in its natural source. Isolated nucleic acid, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "peptide", "polypeptide" and protein" are used interchangeably herein unless otherwise distinguished to refer to polymers of amino acids of any length. These terms also include proteins that are post-translationally modified through reactions that include glycosylation, acetylation and phosphorylation.

By "growth factor" is meant an agent that, at least, promotes cell growth or induces phenotypic changes.

The term "angiogenic" means an agent that alone or in combination with other agents induces angiogenesis, and includes, but is not limited to, fibroblast growth factor (FGF), vascular endothelial growth factor (VEGF), hepatocyte growth factor, angiogenin, transforming growth factor (TGF), tissue necrosis factor (TNF, e.g., TNF-α), platelet derived growth factor (PDGF), granulocyte colony stimulatory factor (GCSF), placental GF, IL-8, proliferin, angiopoietin, e.g., angiopoietin-1 and angiopoietin-2, thrombospondin, ephrin-A1, E-selectin, leptin and heparin affinity regulatory peptide.

"Gene regulation" or "gene regulatory therapy" as used herein includes delivery of one or more gene regulatory stimulations to regulate gene expression in an expression cassette. The gene regulatory stimulations include stimulations that trigger a transcriptional control element, e.g., a promoter.

A "user" includes a physician or other caregiver using a gene regulatory system to treat a patient.

Gene Delivery Vehicles and Control of Gene Expression

The methods and apparatus of the invention include the use of recombinant virus or genetically modified cells to deliver genes to an animal, the expression of which in vivo prevents, inhibits or treats at least one symptom of a particular condition. The exogenously delivered gene includes at least one open reading frame encoding a gene product operably linked to at least one regulatable transcription control element. The methods and apparatus also employ a gene regulatory stimulator that emits a stimulation including, but not limited to, light of a particular wavelength or a range of wavelengths, light of a particular energy, an electric field, or other forms of temperature or matter, which stimulation is recognized by the regulatable transcription control element. A regulatable transcriptional control element includes a promoter, e.g., an inducible or repressible promoter, an enhancer, or a combination thereof. For instance, the promoter may be responsive to certain wavelengths of light. However, the invention is not limited to a particular combination of regulatory stimulation and regulatory element.

A. Regulatable Transcription Control Elements

A variety of strategies have been devised to control expression of transferred genes and thus alter the pharmacokinetics of vectors in the context of regulatable or inducible transcription control elements. Many of these regulatable promoters use exogenously administered agents to control transgene expression and some use the physiologic milieu to control gene expression. Examples of the exogenous control promoters include the tetracycline-responsive promoter, a chimeric transactivator consisting of the DNA and tetracycline-binding domains from the bacterial tet repressor fused to the transactivation domain of herpes simplex virion protein 16; a chimeric promoter with multiple cyclic adenosine monophosphate response elements superimposed on a minimal fragment of the 5'-flanking region of the cystic fibrosis transmembrane conductance regulator gene; the EGR1 radiation-inducible promoter; and the chimeric GRE promoter (Lee et al., *J. Thoracic Cardio. Surg.*, 118:26 (1996)), with 5 GREs from the rat tyrosine aminotransferase gene in tandem with the insertion of Ad2 major late promoter TATA box-initiation site (Narumi et al., *Blood*, 92:812 (1998)). Examples of the physiologic control of promoters include a chimera of the thymidine kinase promoter and the thyroid hormone and retinoic acid-responsive element responsive to both exogenous and endogenous tri-iodothyronine (Hayashi et al., *J. Biol. Chem.*, 269:23872 (1994)); complement factor 3 and serum amyloid A3 promoters responsive to inflammatory stimuli; the grp78 and BiP stress-inducible promoter, a glucose-regulated protein that is inducible through glucose deprivation, chronic anoxia, and acidic pH (Gazit et al., *Cancer Res.*, 55:1660 (1995)); and hypoxia-inducible factor 1 and a heterodimeric basic helix-loop-helix protein that activates transcription of the human erythropoietin gene in hypoxic cells, which has been shown to act as a regulatable promoter in the context of gene therapy in vivo (Forsythe et al., *Mol. Cell Biol.*, 16:4604 (1996)).

Regulatable transcription control elements useful in devices and methods of the invention include, but are not limited to, a truncated ligand binding domain of a progesterin receptor (controlled by antiprogestin), a tet promoter (controlled by tet and dox) (Dhawan et al., *Somat. Cell. Mol. Genet.*, 21, 233 (1995); Gossen et al., *Science*, 268:1766 (1995); Gossen et al., *Science*, 89:5547 (1992); Shockett et al., *Proc. Natl. Acad. Sci. USA*, 92, 6522 (1995)), hypoxia-inducible nuclear factors (Semenza et al., *Proc. Natl. Acad. Sci. USA*, 88, 5680 (1991); Semenza et al., *J. Biol. Chem.*, 269, 23757)), steroid-inducible elements and promoters, such as the glucocorticoid response element (GRE) (Mader and White, *Proc. Natl. Acad. Sci. USA*, 90, 5603 (1993)), and the fusion consensus element for RU486 induction (Wang et al., *Proc. Natl. Acad. Sci. USA*, 91:818 (1994)), those sensitive to electromagnetic fields, e.g., those present in metallothionein I or II, c-myc, and HSP70 promoters (Lin et al., *J. Cell. Biochem.*, 81:143 (2001); Lin et al., *J. Cell. Biochem.*, 54:281 (1994); U.S. published application 20020099026)), and electric pulses (Rubenstrunk et al., *J. Gene Med.*, 5:773 (2003)), as well as a yeast GAL4/TATA promoter, auxin inducible element, an ecdysone responsive element (No et al., *Proc. Natl. Acad. Sci. USA*, 93:3346 (1996)), an element inducible by rapamycin (FK506) or an analog thereof (Rivera et al., *Nat. Med.*, 2:1028 (1996); Ye et al., *Science* 283:88 (1999); Rivera et al., *Proc. Natl. Acad. Sci. USA*, 96:8657 (1999)), a tat responsive element, a metal, e.g., zinc, inducible element, a radiation inducible element, e.g., ionizing radiation has been used as the inducer of the promoter of the early growth response gene (Erg-1) (Hallahan et al., *Nat. Med.*, 1:786 (1995)), an element which binds nuclear receptor PPARγ (peroxisome proliferators activated receptors), which is composed of a minimal promoter fused to PPRE (PPAR responsive elements, see WO 00/78986), a cytochrome P450/A1 promoter, a MDR-1 promoter, a promoter induced by specific cytokines (Varley et al., *Nat. Biotech.*, 15:1002 (1997)), a light inducible element (Shimizu-Sato et al., *Nat. Biotech.*, 20:1041 (02002)), a lacZ promoter, and a yeast Leu3 promoter.

In some embodiments, cell- or tissue-specific control elements, such as muscle-specific and inducible promoters, enhancers and the like, will be of particular use, e.g., in conjunction with regulatable transcriptional control elements. Such control elements include, but are not limited to, those derived from the actin and myosin gene families, such as from the myoD gene family (Weintraub et al., *Science*, 251, 761 (1991)); the myocyte-specific enhancer binding factor MEF-2 (Cserjesi and Olson, *Mol. Cell Biol.*, 11, 4854 (1991)); control elements derived from the human skeletal actin gene (Muscat et al., *Mol. Cell Bio.*, 7, 4089 (1987)) and the cardiac actin gene; muscle creatine kinase sequence elements (Johnson et al., *Mol. Cell Biol.*, 9, 3393 (1989)) and the murine creatine kinase enhancer (mCK) element; control elements derived from the skeletal fast-twitch troponin C gene, the slow-twitch cardiac troponin C gene and the slow-twitch troponin I genes.

Cardiac cell restricted promoters include but are not limited to promoters from the following genes: a α-myosin heavy chain gene, e.g., a ventricular α-myosin heavy chain gene, β-myosin heavy chain gene, e.g., a ventricular β-myosin heavy chain gene, myosin light chain 2v gene, e.g., a ventricular myosin light chain 2 gene, myosin light chain 2a gene, e.g., a ventricular myosin light chain 2 gene, cardiomyocyte-restricted cardiac ankyrin repeat protein (CARP) gene, cardiac α-actin gene, cardiac m2 muscarinic acetylcholine gene, ANP gene, BNP gene, cardiac troponin C gene, cardiac troponin I gene, cardiac troponin T gene, cardiac sarcoplasmic reticulum Ca-ATPase gene, skeletal α-actin gene, as well as an artificial cardiac cell-specific promoter.

The response of the regulatable transcription control element to one or more intermittent stimulations, a prolonged stimulation or different levels of a stimulation, may be tested in vitro or in vivo. The vector may include the regulatable transcriptional control element linked to a marker gene, i.e., one which is readily detectable or capable of detection such as green fluorescent protein (GFP). For example, a vector having a promoter which is sensitive to electrical pulses, a MT-I or MT-II promoter (Rubenstruck et al., *J. Gene Med.*, 5:773 (2003)), is linked to an open reading frame for a marker gene. The resulting expression cassette, e.g., one which is introduced to an adenovirus vector or to a plasmid vector, is employed to infect or transfect murine cells, e.g., murine cardiac cells, or heart sections. An electrode system designed for use in a small flask is used to deliver electrical pulses. Then fluorescence in the cells or a lysate thereof is detected, and/or or vector specific RNA is measured, for instance, using RT-PCR, and optionally compared to data from control cells. Similarly, a vector having a promoter which is sensitive to electrical pulses is linked to an open reading frame for a therapeutic gene, and the phenotype of the recombinant cells compared to control cells. Vectors may also be introduced to a non-human large animal model, e.g., pigs, to determine the level and spatial expression of the exogenously introduced gene in response to stimulations, e.g., electrical pulses, from an implantable device in that animal.

B. Gene Delivery Vehicles

The exogenous gene may be present in a recombinant virus, isolated nucleic acid or donor cells. Sources for donor cells include but are not limited to bone marrow-derived cells, e.g., mesenchymal cells and stromal cells, smooth muscle cells, fibroblasts, SP cells, pluripotent cells or totipotent cells, e.g., teratoma cells, hematopoietic stem cells, for instance, cells from cord blood and isolated CD34+ cells, multipotent adult progenitor cells, adult stem cells, embryonic stem cells, skeletal muscle derived cells, for instance, skeletal muscle cells and skeletal myoblasts, cardiac derived cells, myocytes, e.g., ventricular myocytes, atrial myocytes, SA nodal myocytes, AV nodal myocytes, and Purkinje cells. In one embodiment, the donor cells are autologous cells, however, non-autologous cells, e.g., xenogeneic cells, may be employed. The donor cells can be expanded in vitro to provide an expanded population of donor cells for administration to a recipient animal. In addition, donor cells may be treated in vitro as exemplified below. Sources of donor cells and methods of culturing those cells are known to the art.

Donor cells may be treated in vitro by subjecting them to mechanical, electrical, or biological conditioning, or any combination thereof, as described in U.S. patent application Ser. No. 10/722,115, entitled "METHOD AND APPARATUS FOR CELL AND ELECTRICAL THERAPY OF LIVING TISSUE", which is incorporated by reference herein, conditioning which may include continuous or intermittent exposure to the exogenous stimuli. For instance, biological conditioning includes subjecting donor cells to exogenous agents, e.g., differentiation factors, growth factors, angiogenic proteins, survival factors, and cytokines, as well as to expression cassettes including transgenes encoding a gene product including, but not limited to, an angiogenic protein, a growth factor, a differentiation factor, a survival factor, or a cytokine, and the like. In one embodiment, donor cells, e.g., autologous or nonautologous cells, such as autologous mesenchymal stem cells, are genetically modified for use in the system of the invention ex vivo by introducing an expression cassette containing a regulatable transcription control element linked to a desirable open reading frame, for example, an open reading frame for a prosurvival factor, to those cells. In another embodiment, donor cells are genetically modified in vivo, for instance, by employing recombinant virus and donor cells.

A vector having a transgene, or optionally a combination of vectors, each with a different transgene or a vector with at least two transgenes, can be delivered to one type of donor cell or to different donor cells, which may be introduced to the same gene depository or to different gene depositories on the same device. Delivery of transgenes may be accomplished by any means, e.g., transfection with naked DNA, e.g., a vector comprising the transgene, liposomes, calcium-mediated transformation, electroporation, or transduction, e.g., using recombinant viruses, for instance, via adenovirus, adeno-associated virus, retrovirus or lentivirus vectors. A number of transfection techniques are generally known in the art. See, e.g., Graham et al., *Virology*, 52, 456 (1973), Sambrook et al., *Molecular Cloning: A Laboratory Manual*, Cold Spring Harbor Laboratories, New York (1989), Davis et al., *Basic Methods in Molecular Biology*, Elsevier (1986) and Chu et al., *Gene*, 13, 197 (1981). Particularly suitable transfection methods include calcium phosphate co-precipitation (Graham et al., *Virol.*, 52, 456 (1973)), direct microinjection into cultured cells (Capecchi,*Cell*, 22, 479 (1980)), electroporation (Shigekawa et al.,*BioTechniques*, 6, 742 (1988)), liposome-mediated gene transfer (Mannino et al., *BioTechniques*, 6, 682 (1988)), lipid-mediated transduction (Felgner et al., *Proc. Natl. Acad. Sci. USA*, 84, 7413 (1987)), and nucleic acid delivery using high-velocity microprojectiles (Klein et al., *Nature*, 327, 70 (1987)). Preferred recombinant viruses to deliver exogenous transgenes to donor or host cells include recombinant lentiviruses, retroviruses, adenoviruses, adeno-associated viruses (AAV), and herpes viruses including cytomegalovirus.

Vectors within the scope of the invention include, but are not limited to, isolated nucleic acid, e.g., plasmid-based vectors which may be extrachromosomally maintained, and viral vectors, e.g., recombinant adenovirus, retrovirus, lentivirus, herpesvirus, poxvirus, papilloma virus, or adeno-associated virus, including viral and non-viral vectors which are present in liposomes and other lipid-containing complexes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes, and other macromolecular complexes capable of mediating delivery of a gene to a host cell. By way of illustration, liposomes and other lipid-containing delivery complexes can be used with the virus or isolated nucleic acid at the invention. The principles of the preparation and use of such complexes for gene delivery have been described in the art (see, e.g., Ledley, *Human Gene Therapy*, 6:1129 (1995); Miller et al., *FASEB Journal*, 9:190 (1995); Chonn et al., *Curr. Opin. Biotech.*, 6:698 (1995); Schofield et al., *British Med. Bull.*, 51:56 (1995); Brigham et al., *J. Liposome Res.*, 3:31 (1993)).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector by the cell; components that influence localization of the transferred gene within the cell after uptake (such as agents mediating nuclear localization); and components that influence expression of the gene. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., WO 92/08796; and WO 94/28143). Such marker genes can provide an added measure of control that can be advantageous in gene therapy contexts. A large variety of such vectors are known in the art and are generally available.

Retroviral vectors exhibit several distinctive features including their ability to stably and precisely integrate into the host genome providing long-term transgene expression. These vectors can be manipulated ex vivo to eliminate infectious gene particles to minimize the risk of systemic infection and patient-to-patient transmission. Pseudotyped retroviral vectors can alter host cell tropism.

Lentiviruses are derived from a family of retroviruses that include human immunodeficiency virus and feline immunodeficiency virus. However, unlike retroviruses that only infect dividing cells, lentiviruses can infect both dividing and nondividing cells. For instance, lentiviral vectors based on human immunodeficiency virus genome are capable of efficient transduction of cardiac myocytes in vivo. Although lentiviruses have specific tropisms, pseudotyping the viral envelope with vesicular stomatitis virus yields virus with a broader range.

Adenoviral vectors may be rendered replication-incompetent by deleting the early (E1A and E1B) genes responsible for viral gene expression from the genome and are stably maintained into the host cells in an extrachromosomal form. These vectors have the ability to transfect both replicating and nonreplicating cells and, in particular, these vectors have been shown to efficiently infect cardiac myocytes in vivo, e.g., after direction injection or perfusion. Adenoviral vectors have been shown to result in transient expression of therapeutic genes in vivo, peaking at 7 days and lasting approximately 4 weeks. In addition, adenoviral vectors can be produced at very high titers, allowing efficient gene transfer with small volumes of virus.

Recombinant adeno-associated viruses (rAAV) are derived from nonpathogenic parvoviruses, evoke essentially no cellular immune response, and produce transgene expression lasting months in most systems. Moreover, like adenovirus, adeno-associated virus vectors also have the capability to infect replicating and nonreplicating cells and are believed to be nonpathogenic to humans.

Herpes simplex virus 1 (HSV-1) has a number of important characteristics that make it an important gene delivery vector in vivo. There are two types of HSV-1-based vectors: 1) those produced by inserting the exogenous genes into a backbone virus genome, and 2) HSV amplicon virions that are produced by inserting the exogenous gene into an amplicon plasmid that is subsequently replicated and then packaged into virion particles. HSV-1 can infect a wide variety of cells, both dividing and nondividing, but has obviously strong tropism towards nerve cells. It has a very large genome size and can accommodate very large transgenes (>35 kb). Herpesvirus vectors are particularly useful for delivery of large genes.

Plasmid DNA is often referred to as "naked DNA" to indicate the absence of a more elaborate packaging system. Direct injection of plasmid DNA to myocardial cells in vivo has been accomplished. Plasmid-based vectors are relatively nonimmunogenic and nonpathogenic, with the potential to stably integrate in the cellular genome, resulting in long-term gene expression in postmitotic cells in vivo. For example, expression of secreted angiogenesis factors after muscle injection of plasmid DNA, despite relatively low levels of focal transgene expression, has demonstrated significant biologic effects in animal models and appears promising clinically (Isner, *Nature*, 415:234 (2002)). Furthermore, plasmid DNA is rapidly degraded in the blood stream; therefore, the chance of transgene expression in distant organ systems is negligible. Plasmid DNA may be delivered to cells as part of a macromolecular complex, e.g., a liposome or DNA-protein complex, and delivery may be enhanced using techniques including electroporation.

Donor cells, isolated nucleic acid or recombinant virus may be introduced to one or more gene depositories on the body of a lead prior to or after lead implantation. The one or more depositories are formed at least in part of a porous, biocompatible and substantially nonbiodegradable material such as a membrane or mesh that permits relatively small molecules to enter or exit the depositories but does not permit entry of host cells or exit of donor cells. In one embodiment, the porous, biocompatible and substantially nonbiodegradable material which forms part of the depository is suitable as a substrate for donor cell attachment. In one embodiment, the depository may contain, or may be formed from, in addition to the porous material, a separate substrate support for donor cell attachment. In one embodiment, gene depositories are seeded with genetically modified donor cells, e.g., fibroblast cells. If the seeding of the depository is accomplished prior to implantation, the cells may be seeded on the interior or exterior, or both, of the porous material which forms the gene depository. The donor cells release a factor which itself provides a beneficial effect or may induce host cells to release a factor with a beneficial effect.

In another embodiment, the one or more gene depositories are employed to deliver recombinant virus or isolated nucleic acid to endogenous (host) cells that attach to the porous, biocompatible and substantially nonbiodegradable material of the one or more depositories, e.g., fibrosed fibroblast cells. Recombinant viruses include but are not limited to recombinant lentiviruses, retroviruses, adenoviruses, adeno-associated viruses, and herpes viruses. Thus, in one embodiment, the depository is formed of a porous material which allows transmission of virus from inside the depository to endogenous cells outside the depository, e.g., endogenous cells which have attached to the exterior of the porous, biocompatible and substantially nonbiodegradable material of the gene depository. After device placement and endogenous cell growth on the porous material, virus containing an expression cassette of the invention is released from the depository and infects the endogenous cells on the outside of the porous material. In one embodiment, donor cells may be the source of recombinant virus, for instance, replication incompetent virus. In another embodiment, the gene depository includes recombinant virus or includes a biocompatible particle (matrix or capsule) which contains recombinant virus, and the release or diffusion of the virus from the particle permits subsequent infection of donor cells or host cells, such as host fibrosed cells. The host or donor cells having the recombinant virus or nonviral recombinant nucleic acid release a factor which itself provides a beneficial effect or induces host cells to release a factor with a beneficial effect.

The amount of donor cells which are not genetically modified, or vector(s), e.g., genetically modified donor cells, or an acellular form of the vector, e.g., recombinant virus, introduced to the gene depository and the amount of device based stimulation emitted to achieve a particular outcome will vary depending on various factors including, but not limited to, the gene and promoter chosen, the condition, patient specific parameters, e.g., height, weight and age, and whether prevention or treatment is to be achieved. The vector/device system of the invention is amenable to chronic use for prophylactic purposes.

Vectors of the invention may conveniently be provided in the form of formulations suitable for administration. A suitable administration format may best be determined by a medical practitioner for each patient individually, according to standard procedures. Suitable pharmaceutically acceptable carriers and their formulation are described in standard formulations treatises, e.g., Remington's Pharmaceuticals Sciences. Vectors of the present invention may be formulated in solution at neutral pH, for example, about pH 6.5 to about pH 8.5, more preferably from about pH 7 to 8, with an excipient to bring the solution to about isotonicity, for example, 4.5% mannitol or 0.9% sodium chloride, pH buffered with art-known buffer solutions, such as sodium phosphate, that are generally regarded as safe, together with an accepted preservative such as metacresol 0.1% to 0.75%, more preferably from 0.15% to 0.4% metacresol. Obtaining a desired isotonicity can be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions. If desired, solutions of the above compositions can also be prepared to enhance shelf life and stability. Therapeutically useful compositions of the invention can be prepared by mixing the ingredients following generally accepted procedures. For example, the selected components can be mixed to produce a concentrated mixture which may then be adjusted to the final concentration and viscosity by the addition of water and/or a buffer to control pH or an additional solute to control tonicity.

For viral vectors, at least about $10^3$ to $10^7$ viral particles, preferably about $10^9$ viral particles, and more preferably about $10^{11}$ viral particles can be introduced to one or more gene depositories. The number of viral particles may, but preferably does not, exceed $10^{14}$. For delivery of donor cells, from about $10^2$ to $10^{10}$, e.g., from $10^3$ to $10^9$, $10^4$ to $10^8$, or $10^5$ to $10^7$, cells may be introduced to one or more gene depositories. Agents which may enhance cellular function or stimulate angiogenesis, such pyruvate, catecholamine stimulating agents, fibroblast growth factor, e.g., basic fibroblast growth factor, acidic fibroblast growth factor, fibroblast growth factor-4 and fibroblast growth factor-5, epidermal growth factor, platelet-derived growth factor, vascular endothelial growth factor (e.g., $VEGF_{121}$, $VEGF_{145}$, $VEGF_{165}$, $VEGF_{189}$ or $VEGF_{206}$), tissue growth factors and the like, may optionally be present in a gene depository with donor cells or administered separately. For delivery of plasmid DNA alone, or plasmid DNA in a complex with other macromolecules, the amount of DNA to be administered will be an amount which results in a beneficial effect to the recipient. For example, from 0.0001 to 1 mg or more, e.g., up to 1 g, in individual or divided doses, e.g., from 0.001 to 0.5 mg, or 0.01 to 0.1 mg, of DNA can be administered.

One or more suitable unit dosage forms comprising the isolated nucleic acid vector or recombinant virus, which may optionally be formulated for sustained release, can be administered. The formulations may, where appropriate, be conveniently presented in discrete unit dosage forms and may be prepared by any of the methods well known to pharmacy. Such methods may include the step of bringing into association the vector with liquid carriers, solid matrices, semi-solid carriers, finely divided solid carriers or combinations thereof, and then, if necessary, introducing or shaping the product into the desired delivery system.

Pharmaceutical formulations containing the vector can be prepared by procedures known in the art using well known and readily available ingredients. For example, the vector can be formulated with common excipients, diluents, or carriers, and formed into tablets, capsules, suspensions, powders, and the like. The vectors of the invention can also be formulated as elixirs or solutions for convenient oral administration or as solutions appropriate for parenteral administration, for instance by intramuscular, subcutaneous or intravenous routes.

The pharmaceutical formulations of the vectors can also take the form of an aqueous or anhydrous solution or dispersion, or alternatively the form of an emulsion or suspension.

The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint.

When desired, the above-described formulations can be adapted to give sustained release of the active ingredient employed, e.g., by combination with certain hydrophilic polymer matrices, e.g., comprising natural gels, synthetic polymer gels or mixtures thereof.

Additionally, the vectors are well suited to formulation as sustained release dosage forms and the like. The coatings, envelopes, and protective matrices may be made, for example, from polymeric substances, such as polylactide-glycolates, liposomes, microemulsions, microparticles, nanoparticles, or waxes.

The formulations and compositions described herein may also contain other ingredients such as antimicrobial agents, or preservatives. Furthermore, as described herein the active ingredients may also be used in combination with other therapeutic agents or therapies.

C. Exemplary Biocompatible Materials

Biocompatible materials useful in the invention include those that are substantially nonbiodegradable, i.e., those for retention of at least one component of their contents, and those that are biodegradable, i.e., those for sustained release of at least one component of their contents. The biocompatible material may contain, or be embedded and/or coated, with donor cells or recombinant virus, and is suitable for retaining and/or immobilizing donor cells or optionally other agents including other therapeutic agents under physiological conditions for a sustained period of time, e.g., for months or years after implantation. Once donor cells are introduced to, embedded in or applied to a biocompatible material to form a gene depository, it can be coupled to an implantable medical device. Alternatively, the biocompatible material may be first coupled to the implantable medical device and then the donor cells introduced, embedded in or applied thereto.

The biocompatible material may be a semipermeable membrane which allows the transport of low molecular weight substances inward and outward, permitting cell survival and function, and prevent entry and exit of large molecules, e.g., entry of undesirable molecules such as antibodies and immune cells, and the exit of the donor cells. For instance, microcapsules and hollow fibers with a semipermeable wall may be employed. Molecular weight cut offs for the semipermeable membrane may be about 50 to 100 kD. The membrane may be made of any suitable material which is nondegradable and biocompatible, e.g., agarose, polyvinyl alcohol, e.g., cross-linked polyvinyl alcohol, polyacrylates, polyamides, and polyurethane, and including a dialysis membrane, nylon or cellulose, e.g., cellulose acetate or methyl cellulose, including those which are derivatized to decrease degradation in vivo. The semipermeable materials may also be conjugated with heparin and/or polyethylene glycol (PEG) to decrease immunogenic response, blood clotting and cell attachment on the surface. Examples of such enclosures and semipermeable membranes are discussed in U.S. Pat. Nos. 5,593,852; 5,431, 160: 5,372,133; 4,919,141, and 4,703,756.

Biocompatible materials may include polyglycolic acid and derivatives thereof, carboxyl containing polymers, polyorthoesters, polyesters, e.g., hydroxyl containing polyesters, polyurethanes, polyamino acids such as polylysine, lactic/glycolic acid copolymers, polyanhydrides and ion exchange resins such as sulfonated polytetrafluoroethylene, polydimethyl siloxanes (silicone rubber) or combinations thereof. Reactive groups on the polymers, for example, hydroxy or amino groups, can be acetylated (e.g., Polymer-O—C(=O)CH$_3$ or polymer-NR—C(=O)CH$_3$), and those groups can be prepared either before or after polymerization of monomers.

Additionally, the biocompatible material may be formed from natural proteins or materials which optionally may be modified, e.g., crosslinked using a crosslinking agent such as 1-ethyl-3-(3-dimethylamino-propyl)carbodiimide hydrochloride. Such natural materials include polysaccharides, e.g., cellulose including regenerated cellulose (rayon), albumin, collagen, fibrin, alginate, extracellular matrix (ECM), e.g., xenogeneic ECM, hyaluronan, chitosan, gelatin, keratin, potato starch hydrolyzed for use in electrophoresis, and agar-agar (agarose), or other "isolated materials". An "isolated" material has been separated from at least one contaminant structure with which it is normally associated in its natural state such as in an organism or in an in vitro cultured cell population.

In one embodiment, the material may include liposomes, a hydrogel, cyclodextrins, nanocapsules or microspheres. Thus, a biocompatible material includes synthetic polymers in the form of hydrogels or other porous materials, e.g., permeable configurations or morphologies, such as polyvinyl alcohol, polyvinylpyrrolidone and polyacrylamide, polyethylene oxide, poly(2-hydroxyethyl methacrylate); natural polymers such as gums and starches; synthetic elastomers such as silicone rubber, polyurethane rubber; and natural rubbers, and include poly[α(4-aminobutyl)]-1-glycolic acid, polyethylene oxide (Roy et al., Mol. Ther., 7:401 (2003)), poly orthoesters (Heller et al., Adv. Drug Delivery Rev., 54:1015 (2002)), silk-elastin-like polymers (Megeld et al., Pharma. Res., 19:954 (2002)), alginate (Wee et al., Adv. Drug Deliv. Rev., 31:267 (1998)), EVAc (poly(ethylene-co-vinyl acetate), microspheres such as poly (D, L-lactide-co-glycolide) copolymer and poly (L-lactide) and poly glycolide, polydioxenone, poly(N-isopropylacrylamide)-b-poly(D,L-lactide), a soy matrix such as one cross-linked with glyoxal and reinforced with a bioactive filler, e.g., hydroxylapatite, poly(epsilon-caprolactone)-poly(ethylene glycol) copolymers, poly(acryloyl hydroxyethyl) starch, polylysine-polyethylene glycol, an agarose hydrogel, or a lipid microtubule-hydrogel.

In one embodiment, the donor cells or recombinant nucleic acid are encapsulated by, embedded in or applied to a biocompatible material, e.g., a nonbiodegradable or biodegradable material, respectively, including but not limited to hydrogels of poloxamers, polyacrylamide, poly(2-hydroxyethyl methacrylate), carboxyvinyl-polymers (e.g., Carbopol 934, Goodrich Chemical Co.), cellulose derivatives, e.g., methylcellulose, cellulose acetate and hydroxypropyl cellulose, polyvinyl pyrrolidone or polyvinyl alcohols.

In some embodiments, recombinant nucleic acid is embedded in or encapsulated by a biocompatible and biodegradable polymeric such as collagen, fibrin, polyhydroxyalkanoates, cellulose, polylactic-polyglycolic acid, or a polyanhydride.

Other examples include, without limitation, any biocompatible polymer, whether hydrophilic, hydrophobic, or amphiphilic, such as ethylene vinyl acetate copolymer (EVA), polymethyl methacrylate, polyamides, polycarbonates, polyesters, polyethylene, polypropylenes, polystyrenes, polyvinyl chloride, polytetrafluoroethylene, N-isopropylacrylaamide copolymers, poly(ethylene oxide)/poly(propylene oxide) block copolymers, poly(ethylene glycol)/poly(D, L-lactide-co-glycolide) block copolymers, polyglycolide, polylactides (PLLA or PDLA), poly(caprolactone) (PCL), poly(dioxanone) (PPS) or cellulose derivatives such as cellulose acetate. In an alternative embodiment, a biologically derived polymer, such as protein, collagen, e.g., hydroxylated collagen, or fibrin, or polylactic-polyglycolic acid or a polyanhydride, is a suitable polymeric matrix material.

In another embodiment, the biocompatible material includes polyethyleneterephthalate, polytetrafluoroethylene, copolymer of polyethylene oxide and polypropylene oxide, a combination of polyglycolic acid and polyhydroxyalkanoate, or gelatin, alginate, collagen, hydrogels, poly-3-hydroxybutyrate, poly-4-hydroxybutyrate, and polyhydroxyoctanoate, and polyacrylonitrilepolyvinylchlorides.

For anchorage dependent cells which are attached to and/or embedded in (seeded on) a biocompatible material or other substrate, the following polymers may be employed, e.g., natural polymers such as starch, chitin, glycosaminoglycans, e.g., hyaluronic acid, dermatan sulfate and chondroitin sulfate, collagen, and microbial polyesters, e.g., hydroxyalkanoates such as hydroxyvalerate and hydroxybutyrate copolymers, and synthetic polymers, e.g., poly(orthoesters) and polyanhydrides, and including homo and copolymers of glycolide and lactides (e.g., poly(L-lactide, poly(L-lactide-co-D,L-lactide), poly(L-lactide-co-glycolide, polyglycolide and poly(D,L-lactide), poly(D,L-lactide-coglycolide), poly(lactic acid colysine) and polycaprolactone. The incorporation of molecules such as tricalciumphosphate, hydroxyapatite and basic salts into a polymer matrix can alter the degradation and resorption kinetics of the matrix. Moreover, the properties of polymers can be modified using cross-linking agents.

In one embodiment, the biocompatible substrate for donor cells is isolated ECM. ECM may be isolated from endothelial layers of various cell populations, tissues and/or organs, e.g., any organ or tissue source including the dermis of the skin, liver, alimentary, respiratory, intestinal, urinary or genital tracks of a warm blooded vertebrate. ECM employed in the invention may be from a combination of sources. Isolated ECM may be prepared as a sheet, in particulate form, gel form and the like. The preparation and use of isolated ECM in vivo is described in co-pending, commonly assigned U.S. patent application Ser. No. 11/017,237, entitled "USE OF EXTRACELLULAR MATRIX AND ELECTRICAL THERAPY," filed on Dec. 20, 2004, which is hereby incorporated by reference in its entirety.

In another embodiment, the biocompatible material is a synthetic, nonbiodegradable polymer such as polyurethanes, polydimethylsiloxanes (silicone rubbers), ethylene vinyl acetate copolymer (EVA), poly methylmethacrylate, polyamides, polycarbonates, polyesters, polyethylene, polypropylenes, polystyrenes, polyvinyl chloride, polyvinyl alcohols, polytetrafluoroethylene, or cellulose derivatives such as cellulose acetate.

In one embodiment, the biocompatible material acts as a selectively semipermeable membrane such as a dialysis membrane or nylon.

D. Exemplary Regulatory Stimulations

To control expression of the gene(s) in the implanted device, the implantable device includes a gene regulatory stimulation device which emits a stimulation, the amount and/or strength (i.e., amplitude) of which alters expression, e.g., induces expression, of the open reading that is operably linked to the regulatable transcription control element. In one embodiment, the stimulation is emitted upon sensing a physiological parameter or a change in a physiological parameter, or as a result of a command. For instance, the stimulation may be emitted in response to a command from a predetermined program, e.g., a program that directs the timing of stimulation emission, including the length and spacing of stimulation emission, the amplitude of stimulation, or any combination thereof. Thus, the gene regulatory stimulation device in the systems and methods of the invention provides for temporal and/or conditional dosing of the gene product encoded by the open reading frame(s) in a mammal. Exemplary stimulations may be a certain wavelength of light provided by a light emitting diode (LED) or an electric current provided by two or more electrodes. For embodiments where light is the stimulation and the gene regulatory stimulator(s) is outside of the gene depository, the porous material forming at least part of the gene depository allows for transmission of the light, i.e., the material is transparent or translucent. For embodiments where an electric current is the stimulation and the gene regulatory stimulator(s) is within the gene depository, the porous material includes a conductive component that electrically isolates the virus or cells in the gene depository from electrical stimulation from pacing the heart and electrically isolates the host (endogenous) cells from the electrical stimulation by the gene regulatory stimulator. In one embodiment, the stimulation is emitted for a predetermined time period. Thus, gene expression may be turned on and off or titrated by controlling stimulations emitted by the device.

The regulatory stimulation, and thus the released (excreted, secreted or otherwise cell-free) factor, in accordance with the present invention may be continuous or intermittent, depending, for example, upon the recipient's physiological condition, whether the purpose of the administration is therapeutic or prophylactic, and other factors known to skilled practitioners. The administration may be essentially continuous over a preselected period of time or may be in a series of spaced doses.

E. Exemplary Systems

In one embodiment, the invention provides for a system having a lead with one or more gene depositories positioned at one or more sites along the lead body. In one embodiment, the device is part of a transvenous system. The gene depository may contain genetically modified autologous cells having an expression cassette with a regulatable transcription control element, e.g., a promoter, that is capable of regulating expression of a linked open reading frame or autologous cells having an endogenous gene with a regulatable transcription control element, e.g., a promoter, that is capable of regulating expression of a linked open reading frame. The transcription regulatory control element is responsive to a stimulation provided by a gene regulatory stimulation device located within or in close proximity to the depository. In one embodiment, the gene depositories may contain unmodified donor cells, e.g., dermal or cardiac fibroblasts, endothelial or epithelial cells, having one or more endogenous genes which are responsive to a stimulation provided by a gene regulatory stimulation device located within or in close proximity to the depository. For instance, heme oxygenase (HO-1) expression may be upregulated by light stimulation of 400 to 500 nm, e.g., light between 450 and 490 nm and having a peak at about 470 nm, by a LED with a wavelength band at 50% power of 30 to 50 nm, which expression in turn may alter apoptosis, inflammation and oxidative stress associated with disease or injury. In another embodiment, serpinB2 (plasminogen activator inhibitor 2, PAI-2) expression may be upregulated by light stimulation of 400 to 500 nm, e.g., light between 450 and 490 nm and having a peak at about 470 nm, by a LED with a wavelength band at 50% power of 30 to 50 nm, which expression in turn may alter coagulation, complement activation, inflammation, fibrinolysis, and angiogenesis.

The gene depositories in the lead may be loaded with recombinant virus or cells prior to implant. For example, a biodegradable particle containing recombinant virus may be introduced to one or more gene depositories prior to implant. After implantation, the particle degrades over time and thus releases recombinant virus. The recombinant virus, once released, may infect endogenous cells of the host mammal, e.g., those which are attached to the porous, biocompatible and nonbiodegradable material, so long as the material permits virus passage. In another embodiment, the recombinant virus may infect donor cells which are present in the depository. In another embodiment, recombinant virus or donor cells may be introduced to one or more gene depositories after lead implantation. In this embodiment, one or more lumens in the lead may be employed to deliver recombinant virus or cells to the depositories (see FIG. 3). In an example, recombinant virus or cells may be introduced into housing in a manner similar to that used to fill drug pumps, and pumped through a lumen in the lead. Alternatively, recombinant virus or cells may be introduced through a port into one or more lumens in the lead. For example, a needle and syringe may be employed to access the port.

For instance, the invention provides an implantable device system including a lead containing donor cells, e.g., genetically modified cells, in a gene depository having a porous membrane for inflow of nutrient media and outflow of expressed factors and a stimulation source for gene stimulation within a confined space (a gene regulatory stimulator) which is in close proximity or within to the gene depository. The system includes leads such as endocardial left-sided leads (arterial), transvenous left-sided leads, endocardial right-sided leads, epicardial left-sided leads, and epicardial right-sided leads. In one embodiment, the system includes a transvenous lead. After the lead is placed in the heart, e.g., a left ventricle lead, a regulatory stimulation is delivered by a gene delivery regulatory stimulation device in the lead so as to increase expression of a gene product such as a prosurvival factor, which itself or a gene product induced thereby is released into the extracellular environment and passes through the porous, biocompatible and substantially nonbiodegradable material, thereby entering the patient's blood. In particular, the presence of the prosurvival factor in the patient's heart can result in enhanced repair of infarcted myocardium, enhanced reverse remodeling, enhanced preconditioning of the heart for ischemia and/or normalized cardiac performance. The presence of prosurvival factors during ischemic events, e.g., a hypoxic environment, may reduce infarct size and preserve LV function.

F. Exemplary Gene Regulatory Stimulations, Genes and Delivery Vectors

In one embodiment, an implantable device detects decreased cardiac function, e.g., decreased heart rate variability (HRV) or decreased cardiac output. Upon detection of decreased cardiac function, a gene regulatory stimulator emits a signal, for example, a light which induces expression from a regulatable promoter. For instance, an appropriate stimulation is emitted via a fiber optic or LED. In one embodiment, the light emitted is not monochromatic, but may be centered at a given wavelength and have a bandwidth of 10 or more nm, e.g., 30 nm, at 50% power. The light stimulation results in expression of the open reading frame in an amount effective to enhance cardiac function. In another embodiment, the gene depository includes a promoter sensitive to a subthreshold (below threshold for muscular excitation), threshold, or suprathreshold voltage, or a combination thereof, e.g., a MT1 promoter. Upon detection of decreased cardiac function, the gene regulatory stimulator emits a voltage which induces expression from the promoter. The stimulation is emitted so as to express the open reading frame in an amount effective to enhance cardiac function.

For instance, the open reading frame may encode a gene product that regulates expression of a prosurvival gene product. In one embodiment, recombinant virus or donor cells have an expression cassette which includes a regulatable promoter linked to an open reading frame for MT1. After transcription from the regulatable promoter is altered in response to an appropriate stimulation, e.g., transcription from the regulatable promoter is increased, MT1 is expressed and activates a promoter, e.g., one linked to an open reading frame for Akt1, a prosurvival gene, or a homologous open reading frame. Alternatively, two expression cassettes are employed. The first expression cassette contain a regulatable transcription control element, e.g., one responsive to electrical stimulation, linked to an open reading frame encoding a protein that regulates a different promoter linked to a desirable open reading frame. In another embodiment, the expression cassette includes DNA having a regulatable promoter linked to the Akt1 open reading frame and, after transcription from the regulatable promoter is altered, e.g., increased, Akt1 expression is upregulated. In one embodiment, the expression of the open reading frame enhances preconditioning of the heart for ischemia, enhances repair of infarcted myocardial tissue, and/or enhances reverse modeling and normalization of cardiac performance.

In one embodiment, to prevent or inhibit damage due to myocardial ischemia or a myocardial infarction, vectors are employed that encode gene products that enhance preconditioning of the heart or repair of myocardium. For instance, in one embodiment, a replication incompetent viral vector, e.g., an adenoviral vector, which contains a Akt1 gene operably linked to regulatable promoter is employed to infect autologous donor cells ex vivo to yield genetically modified donor cells, e.g., genetically modified autologous cells such as stem, fibroblast or vascular cells. Those cells may be expanded and/or subjected to conditioning prior to introduction to a gene depository. In vitro cultured cells may be conditioned in vitro, e.g., subjected to hypoxic conditions. The cells may be seeded onto a substrate and optionally further cultured in vitro prior to introduction to a depository. The genetically modified cells may be introduced prior to implantation of the device, or introduced to the one or more depositories via one or more lumens prior to or after device implantation. In one embodiment, the regulatable transcription control element is regulated by a light sensitive promoter. For instance, the open reading frame may be from a prosurvival gene, such as the Akt1 gene. Genetically modified donor cells with an expression cassette which includes a regulatable transcription control region linked to an open reading frame for Akt1 are introduced to depositories in a lead. Upon stimulation emission from gene regulatory stimulators in the implanted lead, the expression of Akt protein is upregulated, which results in the release of prosurvival factors into the extracellular environment, e.g., into a patient's blood within the heart. For certain expressed factors that circulate throughout the heart, the factors may precondition the heart for ischemia, e.g., reduce infarct size and preserve LV function, aid in the repair of infarcted myocardial tissue, and/or aid in reverse remodeling and the normalization of cardiac performance. As continuous gene expression may stress cells within the reservoirs or result in conditioning of such cells, a stimulation may be emitted for only a short period(s) of time and/or at certain levels.

In another embodiment, the gene depository on a transvenous lead includes a recombinant virus having an expression cassette which includes an open reading frame for a desirable gene product operably linked to a regulatable transcription control element. In one embodiment, the recombinant virus is within a biodegradable particle in the depository and the porous, biocompatible and substantially nonbiodegradable material in the gene depository allows for transmission of recombinant virus across the material. In one embodiment, the recombinant virus is replication incompetent. Thus, over time, the virus is released from the particle and passes through the porous, biocompatible and substantially nonbiodegradable material and infects fibroblast cells that have attached to the outside of the porous, biocompatible and substantially nonbiodegradable material after device implantation. Expression from the expression cassette in virally infected cells is controlled by a stimulation from a gene regulatory stimulator which is associated with the depository, such as light from an LED, in the implantable device. Thus, in one embodiment, the porous biocompatible material promotes endogenous fibroblast attachment on the exterior of the depository.

FIG. 1 is a schematic drawing illustrating portions of a system 100 and an environment in which system 100 may be used. In FIG. 1, system 100 includes an implantable medical device (IMD) 102, such as a pulse generator, which is coupled via a lead 104 to tissue, for example, a heart 106 of a human or other mammal. The IMD 102 may be implanted subcutaneously, in a chest, abdomen, or elsewhere.

The IMD 102 is intended to generically represent any type of generator for delivery of electrical stimulation (e.g., pacing, defibrillation, or cardioversion) to, and/or sensing intrinsic or responsive activity of, the heart 106. The IMD 102 represents an example of, among other things, one or a combination of a pacemaker, a cardiac resynchronization therapy (referred to as "CRT") device, a defibrillator, and a cardioverter. In one example, the IMD 102 is a pacemaker. Pacemakers may also coordinate atrial and ventricular contractions to improve heart pumping efficiency.

In another example, the IMD 102 is a CRT device for coordinating the spatial nature of heart depolarizations for improving heart pumping efficiency, such as for subjects experiencing CHF. In yet another example, the IMD 102 is a defibrillator that is capable of delivering higher energy electrical stimuli to a heart (as compared with, for example, pacing pulses). Defibrillators may include cardioverters, which synchronize the delivery of such stimuli to sensed intrinsic heart activity stimulations.

The IMD 102 further optionally includes a controller 103, where the controller 103 can be pre-programmed with commands to regulate the lead 104, including the cardiac stimulator, and can provide a regulatory stimulation or cardiac stimulation. In this example, system 100 also includes an optional external programmer 110 adapted to provide wireless communication with the IMD 102, such as by using a telemetry device 112. The external programmer 110 can be used to provide commands to the lead 104, or portions thereof. The controller and/or the external programmer can be adapted to control the emission of the regulatory stimulation based on a sensed physiological parameter.

The lead 104 has a lead body 108 that includes a lead proximal end portion 114, which in one example is coupled with the IMD 102 such as via a header. The lead 104 extends from the lead proximal end portion 114 to a lead distal end portion 118, and having an intermediate portion 117 therebetween. The lead distal end portion 118, in one example, is coupled within, on, or about portions of the heart 106.

Figure 4:
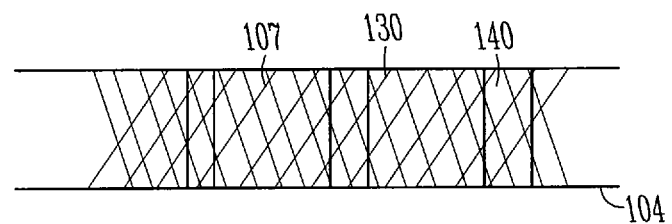
FIG. 4 illustrates an elevational view of a portion of a lead in accordance with at least one embodiment.
Figure 5:
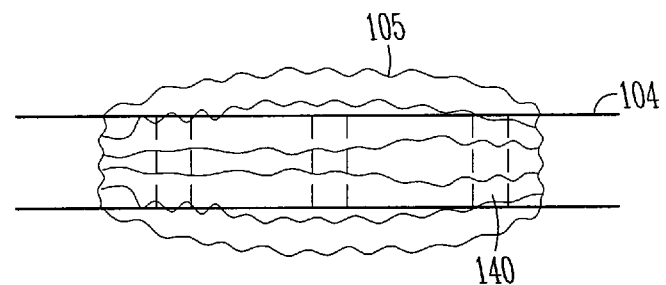
FIG. 5 illustrates an elevational view of a portion of a lead in accordance with at least one embodiment.

The lead 104 further includes one or more gene depositories 130 disposed along the lead body 108, where an example of the one or more gene depositories 130 is shown in greater detail in FIG. 2A. The one or more gene depositories 130 optionally contain various materials, including, but not limited to genetically modified cells 132, such as, but not limited to stem cells, or fibroblasts, as further described above. In another option, the one or more gene depositories 130 can include a virus therein. In one example, donor cells which are not genetically modified or genetically modified donor cells are cultured on to an interior surface and/or exterior surface of the one or more gene depositories 130. Seeding in this manner enables the cells to maintain growth ahead of naturally occurring fibroblast cells that develop after implant. FIGS. 4 and 5 illustrate examples of a lead 104 and one or more gene depositories 130 with cultured cells. In one example, the lead 104 includes a mesh substrate 107 for growing DNA modified fibroblast cells 105 thereon.

The one or more gene depositories 130 allow for the control of gene expression from one or more exogenous genes or unmodified donor cells delivered by the lead, as discussed above in greater detail. The expression of the exogenous or endogenous gene prevents, inhibits or treats at least one symptom of a particular condition, for example, a cardiac condition. In one example, the one or more gene depositories 130 include a material, such as a porous membrane material, that allows for the passage of, for example, a virus, and/or proteins, enzymes, or nutrients, but not cells thereacross. FIG. 2B illustrates another example of the one or more gene depositories 130. In one example, the one or more gene depositories 130 include openings 138, for example slots 139, that allow for transfer of nutrients and enzymes. In another example, the one or more gene depositories include virus and donor cells, where the virus is present in a biodegradable particle and the porous, biocompatible and substantially non-biodegradable material is selected to permit passage of proteins, enzymes, or nutrients, but not cells or the virus thereacross.

Referring again to FIGS. 1 and 2A, the lead 104 further includes one or more gene stimulators 140 that are associated with the one or more gene depositories 130, and where the gene stimulators 140 allow for stimulation of material of the gene depositories 130, for example, the genetically modified cells 132. In one example, the gene stimulator 140 includes any one or more in combination of an LED, an electrode, or others. In one example, the gene stimulator 140 can emit a regulatory stimulation capable of regulating a regulatable transcription control element in an expression cassette. The gene stimulator 140 and the stimulation, energy, or stimulations emitted thereby is controllable, in one example, by the IMD 102. In an example, the gene stimulator is associated with a conduit that allows for energy, such as light, to be transmitted therethrough, for example, from the IMD 102. In yet another example, the control signal is externally delivered. The conduit is, in an example, disposed along the lead body. For example, the conduit is disposed longitudinally along the lead body. In an example, the conduit is a fiber optic wave guide 107 that transmits energy from a source or a light source, for example, an LED disposed within the header of the IMD. In an example, the gene stimulator 140 is controllable by the external programmer 110. In another option, the control signal is applied by placing the lead, or the system, or the patient having the system implanted therein in an external energy field, such as, but not limited to, a light field.

FIG. 3 illustrates another example of a lead 104. The lead includes one or more gene depositories 130 and a gene stimulator associated therewith. The one or more gene depositories include a porous material 142, such as a membrane, that promotes fibroblast cell growth. The porous material 142 is selected to allow the virus to move through the material. In a further option, the porous material 142 is transparent or translucent to light. Disposed within or associated with the one or more gene depositories 130 is a capsule 144, for example, a degradable capsule, containing a virus 146 therein. In one embodiment, before, at time of, or after the time of implant, the virus 146 is inserted into the one or more gene depositories 130. Before the capsule 144 breaks down, fibrotic cells 148 form on to the outside of the gene depositories 130 after implant. The cells 148 form a barrier to the virus 146. The capsule 144 eventually degrades and releases the virus, and infection occurs to the cells 148 that are attached to the exterior of the one or more gene depositories 130.

In another example, the lead 104 includes one or more lumens 113 therein. The one or more lumens allow for the delivery of a virus to an interior portion of the one or more depositories 130. For example, a syringe 190 can be used with an injection portion to introduce the virus 146 into the one or more depositories 130 after an implant. The virus 146 may be delivered within the lead after the fibroblast cells have begun to adhere to the outside of the one or more gene depositories, for example, after several weeks. For example, this can be used when virus viability is limited, especially in the environment of the gene depositories.

The system 100 provides a device that contains genetically engineered cells and a stimulation source for gene stimulation, for example, within a confined space such as a gene depository having material, such as a porous membrane, that allows for inflow of nutrient media and outflow of expressed therapeutic factors.

It is to be understood that the above description is intended to be illustrative, and not restrictive. Although the use of the implantable device has been described for use as a lead in, for example, a cardiac stimulation system, the implantable device could as well be applied to other types of body stimulating systems. Many other embodiments will be apparent to those of skill in the art upon reviewing the above description. The scope should, therefore, be determined with reference to the appended claims, along with the full scope of equivalents to which such claims are entitled.

What is claimed is:

1. A method of using a lead to regulate expression of a soluble cellular protein, comprising:
   a) providing a mammal implanted with i) a system comprising:
   a lead including a lead body extending from a proximal end portion to a distal end portion;
   one or more depositories disposed along and connected to the lead body, the one or more depositories include a porous, biocompatible and substantially nonbiodegradable material, wherein the material is selected to allow the passage of soluble protein expressed by donor cells and prevent passage of the donor cells across the material, wherein the porous, biocompatible and substantially nonbiodegradable material comprises a synthetic polymer or a cross-linked natural polymer; and
   one or more gene regulatory stimulators associated with the one or more depositories, the one or more gene regulatory stimulators emit light of a particular wavelength or light of a particular energy capable of regulating a regulatable transcription control element in an expression cassette including the regulatable transcription control element operably linked to an open reading frame of interest or in an endogenous gene which includes the regulatable transcription control element operably linked to an open reading frame of interest, wherein the open reading frame encodes the soluble protein,
   wherein the one or more depositories comprise donor cells that are not genetically modified but comprise the regulatable transcription control element, donor cells that are genetically modified with the expression cassette, or a combination thereof, or
   ii) a lead comprising:
   a lead body extending from a proximal end portion to a distal end portion and having an intermediate portion therebetween;
   one or more depositories disposed along and connected to the lead body, the one or more depositories include a porous, biocompatible and substantially nonbiodegradable material, wherein the material is selected to allow the passage of soluble protein expressed by donor cells and prevent passage of the donor cells across the material, wherein the porous, biocompatible and substantially nonbiodegradable material comprises a synthetic polymer or a cross-linked natural polymer;
   the one or more depositories having donor cells that are genetically modified with an expression cassette comprising a regulatable transcription control element operably linked to an open reading frame of interest, donor cells which are not genetically modified but which comprise an endogenous gene which includes a regulatable transcription control element operably linked to an open reading frame of interest, or a combination thereof, wherein the open reading frame encodes the soluble protein; and
   one or more gene regulatory stimulators associated with the one or more depositories, the one or more gene regulatory stimulators emit light of a particular wavelength or light of a particular energy capable of regulating the regulatable transcription control element; and
   b) delivering the light from the one or more gene regulatory stimulators to the donor cells which are genetically modified or to the donor cells which are not genetically modified in the one or more depositories in an amount effective to regulate expression of the soluble protein.

2. The method of claim 1, wherein the delivery of the regulatory stimulation is in response to a sensed physiological parameter in the mammal.

3. The method of claim 2, wherein the physiological parameter is sensed by an implanted sensor.

4. The method of claim 1, wherein the delivery of the regulatory stimulation is in response to a command.

5. The method of claim 4, wherein the command is an external command.

6. The method of claim 4, wherein the command is from an implanted programmable device.

7. The method of claim 1, further comprising ceasing delivery of the regulatory stimulation.

8. The method of claim 7, wherein the delivery ceases in response to receiving a command.

9. The method of claim 8, wherein the command is an external command.

10. The method of claim 8, wherein the command is from an implanted programmable device.

11. The method of claim 5 or 9, wherein the external command is entered by at least one of physician or other caregiver, or a patient through an external system.

12. The method of claim 1, wherein the delivery of the regulatory stimulation is in response to a sensed physiological parameter indicative of ischemia, remodeling or myocardial infarction in the mammal.

13. The method of claim 12, wherein the regulatory stimulation is in response to a sensed physiological parameter indicative of ischemia and is delivered in response to a sensed S-T segment deviation from baseline, prolongation of the Q-T interval, T-wave inversion, shortness of breath, chest pain, blood pH of less than 7.0, blood $K^+$ concentration of greater than 10 mM, glucose concentration of less than about 80 mg/dl or greater than about 115 mg/dl, or oxygen concentration of less than about 90% $pO_2$.

14. The method of claim 12, wherein the regulatory stimulation is in response to a sensed physiological parameter indicative of remodeling and is delivered in response to a sensed decrease in ejection fraction or QRS complex width of greater than about 120 msec.

15. The method of claim 1, wherein the regulatory stimulation is in response to a sensed physiological parameter indicative of myocardial infarction and delivered in response to a sensed aberrant electrical activation front, S-T segment elevation, Q wave alteration, reduced R wave amplitude, chest pain or shortness of breath.

16. The method of claim 1, wherein the regulation of the expression prevents, inhibits or treats cardiac ischernia, cardiac remodeling or myocardial infarction in the mammal.

17. The method of claim 1, wherein the regulation of the expression enhances preconditioning of the heart for ischemia, repair of infarcted myocardial tissue, or reverse remodeling in the mammal.

18. The method of claim 1, wherein the delivery of the regulatory stimulation is in response to a sensed worsening of heart failure, atrial fibrillation, ventricular fibrillation, ventricular tachycardia, or bradycardia in the mammal.

19. The method of claim 1, further comprising transmitting light energy from a source via a fiber optic wave guide of the lead.

20. The method of claim 1, further comprising placing the lead within an external energy field.

21. The method of claim 1 wherein the material comprises ethylene vinyl acetate copolymer (EVA), polymethyl methacrylate, polyamides, polycarbonates, polyesters, polyethylene, polypropylenes, polystyrenes, polyvinyl chloride, polytetrafluoroethylene, N-isopropylacrylamide copolymers, poly(ethylene oxide)/poly(propylene oxide) block copolymers, poly(ethylene glycol)/poly(D,L-lactide-co-glycolide) block copolymers, polyglycolide, polylactides (PHA or PDLA), poly(caprolactone) (PCL), poly(dioxanone) (PPS), cellulose or cellulose acetate.

* * * * *